(12) United States Patent
Allis et al.

(10) Patent No.: US 11,724,027 B2
(45) Date of Patent: Aug. 15, 2023

(54) FLUID DELIVERY DEVICE WITH SENSOR

(71) Applicant: Insulet Corporation, Acton, MA (US)

(72) Inventors: Daniel Allis, Boxford, MA (US);
Kenneth Phillips, Boston, MA (US);
Jacob Anthony Coumans, Old Lyme, CT (US)

(73) Assignee: INSULET CORPORATION, Acton, MA (US)

( * ) Notice: Subject to any disclaimer, the term of this patent is extended or adjusted under 35 U.S.C. 154(b) by 483 days.

(21) Appl. No.: 16/884,802

(22) Filed: May 27, 2020

(65) Prior Publication Data
US 2020/0338264 A1   Oct. 29, 2020

Related U.S. Application Data

(63) Continuation of application No. 15/714,496, filed on Sep. 25, 2017, now Pat. No. 10,765,807.
(Continued)

(51) Int. Cl.
*A61M 5/168* (2006.01)
*G16H 20/17* (2018.01)
(Continued)

(52) U.S. Cl.
CPC ...... *A61M 5/16854* (2013.01); *A61M 5/1452* (2013.01); *A61M 5/14248* (2013.01);
(Continued)

(58) Field of Classification Search
CPC .......... A61M 5/16854; A61M 5/14248; A61M 5/1452; A61M 5/16831;
(Continued)

(56) References Cited

U.S. PATENT DOCUMENTS 2,797,149 A * 6/1957 Skeggs ................. G01N 35/08
436/95
3,631,847 A    1/1972 Hobbs
(Continued)

FOREIGN PATENT DOCUMENTS

AU    2015200834 A1    3/2015
CN       1297140 A      5/2001
(Continued)

OTHER PUBLICATIONS

US 5,954,699 A, 09/1999, Jost et al. (withdrawn)
(Continued)

*Primary Examiner* — Nathan R Price
*Assistant Examiner* — Mark A Igel
(74) *Attorney, Agent, or Firm* — Goodwin Procter LLP

(57) ABSTRACT

A wearable drug delivery device for monitoring unintended over-delivery and/or under-delivery of a stored liquid drug are provided. An absolute pressure sensor can be positioned within the fluid path of the drug delivery device. The absolute pressor sensor can detect both ambient pressure (e.g., absolute or atmospheric pressure) and relative pressure (gage or pumping pressure). Based on the detected pressures, the effects of external ambient pressure on air with the fluid path can be determined during both intended drug delivery events and unintended drug delivery events. In turn, under-delivery and/or over-delivery of the liquid drug can be determined. Based on the severity of the determined under-delivery or over-delivery of the liquid drug, alarms indicating different urgencies can be provided to the user.

20 Claims, 11 Drawing Sheets

Related U.S. Application Data

(60) Provisional application No. 62/398,792, filed on Sep. 23, 2016.

(51) Int. Cl.
*A61M 5/142* (2006.01)
*A61M 5/145* (2006.01)

(52) U.S. Cl.
CPC ........ *A61M 5/16831* (2013.01); *G16H 20/17* (2018.01); *A61M 2005/14264* (2013.01); *A61M 2005/16863* (2013.01); *A61M 2205/18* (2013.01); *A61M 2205/3331* (2013.01); *A61M 2205/3334* (2013.01); *A61M 2205/3368* (2013.01); *A61M 2205/3379* (2013.01); *A61M 2205/581* (2013.01); *A61M 2205/582* (2013.01); *A61M 2205/583* (2013.01); *A61M 2205/70* (2013.01)

(58) Field of Classification Search
CPC ......... A61M 2005/14264; A61M 2005/16863; A61M 2005/18; A61M 2005/3331; A61M 2005/3334; A61M 2005/3368; A61M 2005/3379; A61M 2005/581; A61M 2005/582; A61M 2005/583; A61M 2005/70
See application file for complete search history.

(56) References Cited

U.S. PATENT DOCUMENTS

| | | | |
|---|---|---|---|
| 3,634,039 A | | 1/1972 | Brandy |
| 3,812,843 A | | 5/1974 | Wootten et al. |
| 3,841,328 A | | 10/1974 | Jensen |
| 3,963,380 A | * | 6/1976 | Thomas, Jr. ...... A61M 5/14276 600/16 |
| 4,055,175 A | | 10/1977 | Clemens et al. |
| 4,146,029 A | | 3/1979 | Ellinwood, Jr. |
| 4,151,845 A | * | 5/1979 | Clemens ............. A61M 5/1723 128/DIG. 13 |
| 4,245,634 A | | 1/1981 | Albisser et al. |
| 4,368,980 A | | 1/1983 | Aldred et al. |
| 4,403,984 A | * | 9/1983 | Ash .................... A61B 5/14528 600/364 |
| 4,464,170 A | | 8/1984 | Clemens et al. |
| 4,526,568 A | | 7/1985 | Clemens et al. |
| 4,526,569 A | | 7/1985 | Bernardi |
| 4,529,401 A | * | 7/1985 | Leslie ................. A61M 5/1456 604/67 |
| 4,559,033 A | | 12/1985 | Stephen et al. |
| 4,573,968 A | | 3/1986 | Parker |
| 4,633,878 A | | 1/1987 | Bombardieri |
| 4,657,529 A | | 4/1987 | Prince et al. |
| 4,670,007 A | * | 6/1987 | Wheeldon ........... A61M 5/172 128/DIG. 13 |
| 4,743,243 A | | 5/1988 | Vaillancourt |
| 4,755,173 A | | 7/1988 | Konopka et al. |
| 4,781,688 A | | 11/1988 | Thoma et al. |
| 4,781,693 A | | 11/1988 | Martinez et al. |
| 4,854,170 A | | 8/1989 | Brimhall et al. |
| 4,886,499 A | | 12/1989 | Cirelli et al. |
| 4,900,292 A | | 2/1990 | Berry et al. |
| 4,919,596 A | * | 4/1990 | Slate .................... A61M 5/172 417/18 |
| 4,925,444 A | | 5/1990 | Orkin et al. |
| 4,940,527 A | | 7/1990 | Kazlauskas et al. |
| 4,975,581 A | | 12/1990 | Robinson et al. |
| 4,976,720 A | | 12/1990 | Machold et al. |
| 4,981,140 A | | 1/1991 | Wyatt |
| 4,994,047 A | | 2/1991 | Walker et al. |
| 5,007,286 A | * | 4/1991 | Malcolm ................. G01L 9/06 73/861.47 |
| 5,097,834 A | | 3/1992 | Skrabal |
| 5,102,406 A | | 4/1992 | Arnold |
| 5,109,850 A | | 5/1992 | Blanco et al. |
| 5,125,415 A | | 6/1992 | Bell |
| 5,134,079 A | * | 7/1992 | Cusack .................. G01N 35/08 436/52 |
| 5,153,827 A | * | 10/1992 | Coutre ............... A61M 5/1723 604/67 |
| 5,165,406 A | | 11/1992 | Wong |
| 5,176,662 A | | 1/1993 | Bartholomew et al. |
| 5,178,609 A | | 1/1993 | Ishikawa |
| 5,207,642 A | | 5/1993 | Orkin et al. |
| 5,237,993 A | | 8/1993 | Skrabal |
| 5,257,980 A | | 11/1993 | Van Antwerp et al. |
| 5,273,517 A | | 12/1993 | Barone et al. |
| 5,299,571 A | | 4/1994 | Mastrototaro |
| 5,308,982 A | | 5/1994 | Ivaldi et al. |
| 5,342,298 A | * | 8/1994 | Michaels ........ A61M 25/10184 604/920 |
| 5,377,674 A | | 1/1995 | Kuestner |
| 5,380,665 A | * | 1/1995 | Cusack .................. G01N 35/08 422/82 |
| 5,385,539 A | | 1/1995 | Maynard |
| 5,389,078 A | * | 2/1995 | Zalesky ................ A61M 5/172 604/246 |
| 5,421,812 A | * | 6/1995 | Langley ................ A61M 1/303 210/96.1 |
| 5,505,709 A | | 4/1996 | Funderburk et al. |
| 5,505,828 A | | 4/1996 | Wong et al. |
| 5,535,752 A | * | 7/1996 | Halperin .............. A61N 1/3655 600/483 |
| 5,558,640 A | | 9/1996 | Pfeiler et al. |
| 5,569,186 A | | 10/1996 | Lord et al. |
| 5,584,813 A | | 12/1996 | Livingston et al. |
| 5,609,572 A | * | 3/1997 | Lang ................ A61M 5/14224 604/22 |
| 5,665,065 A | | 9/1997 | Colman et al. |
| 5,685,859 A | | 11/1997 | Kornerup |
| 5,693,018 A | | 12/1997 | Kriesel et al. |
| 5,697,899 A | | 12/1997 | Hillman et al. |
| 5,700,695 A | | 12/1997 | Yassinzadeh et al. |
| 5,703,364 A | | 12/1997 | Rosenthal |
| 5,714,123 A | | 2/1998 | Sohrab |
| 5,716,343 A | | 2/1998 | Kriesel et al. |
| 5,722,397 A | | 3/1998 | Eppstein |
| 5,741,228 A | | 4/1998 | Lambrecht et al. |
| 5,746,217 A | | 5/1998 | Erickson et al. |
| 5,755,682 A | | 5/1998 | Knudson et al. |
| 5,758,643 A | | 6/1998 | Wong et al. |
| 5,800,405 A | | 9/1998 | McPhee |
| 5,800,420 A | | 9/1998 | Gross et al. |
| 5,801,057 A | | 9/1998 | Smart et al. |
| 5,804,048 A | | 9/1998 | Wong et al. |
| 5,817,007 A | | 10/1998 | Fodgaard et al. |
| 5,820,622 A | | 10/1998 | Gross et al. |
| 5,823,951 A | | 10/1998 | Messerschmidt |
| 5,840,020 A | | 11/1998 | Heinonen et al. |
| 5,848,991 A | | 12/1998 | Gross et al. |
| 5,851,197 A | | 12/1998 | Marano et al. |
| 5,858,005 A | | 1/1999 | Kriesel |
| 5,865,806 A | | 2/1999 | Howell |
| 5,871,470 A | | 2/1999 | McWha |
| 5,879,310 A | | 3/1999 | Sopp et al. |
| 5,902,253 A | | 5/1999 | Pfeiffer et al. |
| 5,931,814 A | | 8/1999 | Alex et al. |
| 5,932,175 A | | 8/1999 | Knute et al. |
| 5,947,911 A | | 9/1999 | Wong et al. |
| 5,971,941 A | | 10/1999 | Simons et al. |
| 5,993,423 A | | 11/1999 | Choi |
| 5,997,501 A | | 12/1999 | Gross et al. |
| 6,017,318 A | | 1/2000 | Gauthier et al. |
| 6,032,059 A | | 2/2000 | Henning et al. |
| 6,036,924 A | | 3/2000 | Simons et al. |
| 6,040,578 A | | 3/2000 | Malin et al. |
| 6,049,727 A | | 4/2000 | Crothall |
| 6,050,978 A | | 4/2000 | Or et al. |
| 6,058,934 A | | 5/2000 | Sullivan |
| 6,066,103 A | | 5/2000 | Duchon et al. |
| 6,071,292 A | | 6/2000 | Makower et al. |

(56) References Cited

U.S. PATENT DOCUMENTS

| | | | |
|---|---|---|---|
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,157,041 A | 12/2000 | Thomas et al. |
| 6,161,028 A | 12/2000 | Braig et al. |
| 6,162,639 A | 12/2000 | Douglas |
| 6,196,046 B1 | 3/2001 | Braig et al. |
| 6,200,287 B1 * | 3/2001 | Keller .................. A61M 1/3693 604/4.01 |
| 6,200,338 B1 | 3/2001 | Solomon et al. |
| 6,214,629 B1 | 4/2001 | Freitag et al. |
| 6,226,082 B1 | 5/2001 | Roe |
| 6,244,776 B1 | 6/2001 | Wiley |
| 6,261,065 B1 | 7/2001 | Nayak et al. |
| 6,262,798 B1 | 7/2001 | Shepherd et al. |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,309,370 B1 | 10/2001 | Haim et al. |
| 6,312,888 B1 | 11/2001 | Wong et al. |
| 6,334,851 B1 | 1/2002 | Hayes et al. |
| 6,375,627 B1 | 4/2002 | Mauze et al. |
| 6,379,301 B1 | 4/2002 | Worthington et al. |
| 6,402,689 B1 | 6/2002 | Scarantino et al. |
| 6,470,279 B1 | 10/2002 | Samsoondar |
| 6,475,196 B1 | 11/2002 | Vachon |
| 6,477,901 B1 * | 11/2002 | Tadigadapa ............ G01F 1/8404 73/861.352 |
| 6,484,044 B1 | 11/2002 | Lilienfeld-Toal |
| 6,491,656 B1 * | 12/2002 | Morris .................. A61M 1/303 210/321.62 |
| 6,512,937 B2 | 1/2003 | Blank et al. |
| 6,525,509 B1 | 2/2003 | Petersson et al. |
| 6,528,809 B1 | 3/2003 | Thomas et al. |
| 6,540,672 B1 | 4/2003 | Simonsen et al. |
| 6,546,268 B1 | 4/2003 | Ishikawa et al. |
| 6,546,269 B1 | 4/2003 | Kumik |
| 6,553,841 B1 * | 4/2003 | Blouch .................. G01L 21/12 73/753 |
| 6,556,850 B1 | 4/2003 | Braig et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,618,603 B2 | 9/2003 | Varalli et al. |
| 6,633,772 B2 | 10/2003 | Ford et al. |
| 6,645,142 B2 | 11/2003 | Braig et al. |
| 6,653,091 B1 | 11/2003 | Dunn et al. |
| 6,662,030 B2 | 12/2003 | Khalil et al. |
| 6,669,663 B1 | 12/2003 | Thompson |
| 6,678,542 B2 | 1/2004 | Braig et al. |
| 6,699,221 B2 | 3/2004 | Vaillancourt |
| 6,718,189 B2 | 4/2004 | Rohrscheib et al. |
| 6,721,582 B2 | 4/2004 | Trepagnier et al. |
| 6,728,560 B2 | 4/2004 | Kollias et al. |
| 6,740,059 B2 * | 5/2004 | Flaherty ............ A61M 5/14248 607/151 |
| 6,740,072 B2 | 5/2004 | Starkweather et al. |
| 6,751,490 B2 | 6/2004 | Esenaliev et al. |
| 6,758,835 B2 | 7/2004 | Close et al. |
| 6,780,156 B2 | 8/2004 | Haueter et al. |
| 6,810,290 B2 | 10/2004 | Lebel et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,862,534 B2 | 3/2005 | Sterling et al. |
| 6,865,408 B1 | 3/2005 | Abbink et al. |
| 6,890,291 B2 | 5/2005 | Robinson et al. |
| 6,936,029 B2 | 8/2005 | Mann et al. |
| 6,949,081 B1 | 9/2005 | Chance |
| 6,958,809 B2 | 10/2005 | Sterling et al. |
| 6,989,891 B2 | 1/2006 | Braig et al. |
| 6,990,366 B2 | 1/2006 | Say et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis, III et al. |
| 7,060,059 B2 | 6/2006 | Keith et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,128,727 B2 | 10/2006 | Flaherty et al. |
| 7,139,593 B2 | 11/2006 | Kavak et al. |
| 7,139,598 B2 | 11/2006 | Hull et al. |
| 7,144,384 B2 | 12/2006 | Gorman et al. |
| 7,171,252 B1 | 1/2007 | Scarantino et al. |
| 7,190,988 B2 | 3/2007 | Say et al. |
| 7,204,823 B2 | 4/2007 | Estes et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van Den Berghe et al. |
| 7,500,949 B2 | 3/2009 | Gottlieb et al. |
| 7,509,156 B2 | 3/2009 | Flanders |
| 7,547,281 B2 | 6/2009 | Hayes et al. |
| 7,569,030 B2 | 8/2009 | Lebel et al. |
| 7,608,042 B2 | 10/2009 | Goldberger et al. |
| 7,680,529 B2 | 3/2010 | Kroll |
| 7,734,323 B2 | 6/2010 | Blomquist et al. |
| 7,766,829 B2 | 8/2010 | Sloan et al. |
| 7,785,258 B2 | 8/2010 | Braig et al. |
| 7,806,854 B2 | 10/2010 | Damiano et al. |
| 7,806,886 B2 | 10/2010 | Kanderian, Jr. et al. |
| 7,918,825 B2 | 4/2011 | O'Connor et al. |
| 7,946,985 B2 | 5/2011 | Mastrototaro et al. |
| 7,972,296 B2 | 7/2011 | Braig et al. |
| 8,221,345 B2 | 7/2012 | Blomquist |
| 8,251,907 B2 | 8/2012 | Sterling et al. |
| 8,449,524 B2 | 5/2013 | Braig et al. |
| 8,547,239 B2 * | 10/2013 | Peatfield ............ A61M 5/16886 604/890.1 |
| 8,810,394 B2 * | 8/2014 | Kalpin ................ A61M 5/1684 702/50 |
| 9,061,097 B2 | 6/2015 | Holt et al. |
| 9,233,204 B2 | 1/2016 | Booth et al. |
| 9,486,571 B2 | 11/2016 | Rosinko |
| 9,743,224 B2 | 8/2017 | San Vicente et al. |
| 9,980,140 B1 | 5/2018 | Spencer et al. |
| 10,248,839 B2 * | 4/2019 | Levy ...................... G06T 7/187 |

(56) References Cited

U.S. PATENT DOCUMENTS

| | | |
|---|---|---|
| 10,335,464 B1 | 7/2019 | Michelich et al. |
| 10,583,250 B2 | 3/2020 | Mazlish et al. |
| 10,737,024 B2 | 8/2020 | Schmid |
| 10,987,468 B2 | 4/2021 | Mazlish et al. |
| 11,197,964 B2 | 12/2021 | Sjolund et al. |
| 11,260,169 B2 | 3/2022 | Estes |
| 2001/0021803 A1 | 9/2001 | Blank et al. |
| 2001/0034023 A1* | 10/2001 | Stanton, Jr. ............ G16B 20/20 435/6.16 |
| 2001/0034502 A1* | 10/2001 | Moberg ............... A61M 5/1456 604/67 |
| 2001/0051377 A1 | 12/2001 | Hammer et al. |
| 2001/0053895 A1 | 12/2001 | Vaillancourt |
| 2002/0010401 A1 | 1/2002 | Bushmakin et al. |
| 2002/0010423 A1 | 1/2002 | Gross et al. |
| 2002/0016568 A1* | 2/2002 | Lebel ............... A61M 5/14244 128/904 |
| 2002/0040208 A1* | 4/2002 | Flaherty ............ A61M 5/14248 604/67 |
| 2002/0123740 A1* | 9/2002 | Flaherty ............... A61M 5/1452 604/93.01 |
| 2002/0128543 A1 | 9/2002 | Leonhardt |
| 2002/0147423 A1 | 10/2002 | Burbank et al. |
| 2002/0155425 A1 | 10/2002 | Han et al. |
| 2003/0023148 A1 | 1/2003 | Lorenz et al. |
| 2003/0050621 A1 | 3/2003 | Lebel et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0100040 A1 | 5/2003 | Bonnecaze et al. |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0163097 A1 | 8/2003 | Fleury et al. |
| 2003/0195404 A1 | 10/2003 | Knobbe et al. |
| 2003/0208113 A1 | 11/2003 | Mault et al. |
| 2003/0208154 A1* | 11/2003 | Close ............... A61B 5/6849 604/65 |
| 2003/0212379 A1 | 11/2003 | Bylund et al. |
| 2003/0216627 A1 | 11/2003 | Lorenz et al. |
| 2003/0220605 A1* | 11/2003 | Bowman, Jr. ........ A61M 5/145 264/109 |
| 2004/0010207 A1 | 1/2004 | Flaherty et al. |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064259 A1 | 4/2004 | Haaland et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1* | 7/2004 | Moberg ............... A61M 5/1456 604/151 |
| 2004/0147034 A1 | 7/2004 | Gore et al. |
| 2004/0171983 A1* | 9/2004 | Sparks ................ G01F 1/8445 128/DIG. 13 |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0049179 A1 | 3/2005 | Davidson et al. |
| 2005/0065464 A1 | 3/2005 | Talbot et al. |
| 2005/0065465 A1 | 3/2005 | Lebel et al. |
| 2005/0075624 A1* | 4/2005 | Miesel ............... A61M 5/14276 604/151 |
| 2005/0105095 A1 | 5/2005 | Pesach et al. |
| 2005/0137573 A1 | 6/2005 | McLaughlin |
| 2005/0171503 A1 | 8/2005 | Van Den Berghe et al. |
| 2005/0182306 A1 | 8/2005 | Sloan |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1* | 9/2005 | Flaherty ............ A61M 5/14248 604/890.1 |
| 2005/0238507 A1 | 10/2005 | Dilanni et al. |
| 2005/0261562 A1* | 11/2005 | Zhou .................. A61B 5/14865 600/347 |
| 2005/0261660 A1 | 11/2005 | Choi |
| 2005/0277912 A1* | 12/2005 | John ................. A61M 5/16827 604/890.1 |
| 2006/0009727 A1 | 1/2006 | O'Mahony et al. |
| 2006/0079809 A1 | 4/2006 | Goldberger et al. |
| 2006/0100494 A1 | 5/2006 | Kroll |
| 2006/0134323 A1 | 6/2006 | O'Brien |
| 2006/0167350 A1 | 7/2006 | Monfre et al. |
| 2006/0173406 A1 | 8/2006 | Hayes et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0270983 A1* | 11/2006 | Lord ................. A61M 5/14276 604/131 |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0106135 A1 | 5/2007 | Sloan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0173761 A1 | 7/2007 | Kanderian et al. |
| 2007/0173974 A1 | 7/2007 | Lin |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1* | 10/2007 | Rosero ..................... A61P 3/10 435/14 |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0078400 A1 | 4/2008 | Martens et al. |
| 2008/0097289 A1 | 4/2008 | Steil et al. |
| 2008/0132880 A1 | 6/2008 | Buchman |
| 2008/0161664 A1 | 7/2008 | Mastrototaro et al. |
| 2008/0172026 A1 | 7/2008 | Blomquist |
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0206067 A1* | 8/2008 | De Corral ........... F04B 11/0075 700/282 |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0269585 A1 | 10/2008 | Ginsberg |
| 2008/0269723 A1 | 10/2008 | Mastrototaro et al. |
| 2008/0287906 A1 | 11/2008 | Burkholz et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |

(56) References Cited

U.S. PATENT DOCUMENTS

| | | |
|---|---|---|
| 2009/0043240 A1 | 2/2009 | Robinson et al. |
| 2009/0054753 A1 | 2/2009 | Robinson et al. |
| 2009/0069743 A1 | 3/2009 | Krishnamoorthy et al. |
| 2009/0069787 A1 | 3/2009 | Estes et al. |
| 2009/0099521 A1 | 4/2009 | Gravesen et al. |
| 2009/0131861 A1 | 5/2009 | Braig et al. |
| 2009/0156922 A1 | 6/2009 | Goldberger et al. |
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |
| 2010/0057042 A1* | 3/2010 | Hayter ............... A61B 5/1486 604/504 |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0152658 A1 | 6/2010 | Hanson et al. |
| 2010/0211003 A1* | 8/2010 | Sundar ................ A61M 5/172 604/67 |
| 2010/0295686 A1 | 11/2010 | Sloan et al. |
| 2011/0054390 A1 | 3/2011 | Searle et al. |
| 2011/0054399 A1 | 3/2011 | Chong et al. |
| 2011/0124996 A1 | 5/2011 | Reinke et al. |
| 2011/0144586 A1 | 6/2011 | Michaud et al. |
| 2011/0160652 A1 | 6/2011 | Yodat et al. |
| 2011/0178472 A1 | 7/2011 | Cabiri |
| 2011/0190694 A1* | 8/2011 | Lanier, Jr. ......... A61M 5/14248 604/67 |
| 2011/0202005 A1* | 8/2011 | Yodfat ............... A61M 5/14248 604/151 |
| 2011/0218495 A1* | 9/2011 | Remde ................ G16H 20/17 604/151 |
| 2011/0230833 A1 | 9/2011 | Landman et al. |
| 2011/0251509 A1 | 10/2011 | Beyhan et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0030393 A1 | 2/2012 | Ganesh et al. |
| 2012/0053556 A1 | 3/2012 | Lee |
| 2012/0078067 A1 | 3/2012 | Kovatchev et al. |
| 2012/0078161 A1 | 3/2012 | Masterson et al. |
| 2012/0078181 A1* | 3/2012 | Smith .................. H02J 7/0029 604/404 |
| 2012/0101451 A1* | 4/2012 | Boit .................... A61M 39/223 417/490 |
| 2012/0190955 A1 | 7/2012 | Rao et al. |
| 2012/0203178 A1 | 8/2012 | Tverskoy |
| 2012/0226259 A1 | 9/2012 | Yodfat et al. |
| 2012/0238851 A1 | 9/2012 | Kamen et al. |
| 2012/0271655 A1 | 10/2012 | Knobel et al. |
| 2012/0277668 A1 | 11/2012 | Chawla |
| 2012/0282111 A1* | 11/2012 | Nip ..................... F04B 43/04 417/48 |
| 2012/0295550 A1 | 11/2012 | Wilson et al. |
| 2013/0030358 A1 | 1/2013 | Yodfat et al. |
| 2013/0178791 A1 | 7/2013 | Javitt |
| 2013/0253472 A1 | 9/2013 | Cabiri |
| 2013/0296823 A1 | 11/2013 | Melker et al. |
| 2013/0317753 A1* | 11/2013 | Kamen ................ H04L 45/02 600/595 |
| 2013/0338576 A1* | 12/2013 | O'Connor .......... A61M 5/14244 604/67 |
| 2014/0005633 A1 | 1/2014 | Finan |
| 2014/0066886 A1 | 3/2014 | Roy et al. |
| 2014/0074033 A1 | 3/2014 | Sonderegger et al. |
| 2014/0128839 A1 | 5/2014 | Dilanni et al. |
| 2014/0135880 A1 | 5/2014 | Baumgartner et al. |
| 2014/0146202 A1 | 5/2014 | Boss et al. |
| 2014/0200426 A1 | 7/2014 | Taub et al. |
| 2014/0230021 A1 | 8/2014 | Birtwhistle et al. |
| 2014/0276554 A1 | 9/2014 | Finan et al. |
| 2014/0276556 A1* | 9/2014 | Saint .................. A61B 5/14532 604/504 |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0120317 A1 | 4/2015 | Mayou et al. |
| 2015/0134265 A1 | 5/2015 | Kohlbrecher et al. |
| 2015/0165119 A1 | 6/2015 | Palerm et al. |
| 2015/0173674 A1 | 6/2015 | Hayes et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0351671 A1 | 12/2015 | Vanslyke et al. |
| 2015/0366945 A1 | 12/2015 | Greene |
| 2016/0015891 A1 | 1/2016 | Papiorek |
| 2016/0038673 A1 | 2/2016 | Morales |
| 2016/0038689 A1 | 2/2016 | Lee et al. |
| 2016/0051749 A1 | 2/2016 | Istoc |
| 2016/0089494 A1 | 3/2016 | Guerrini |
| 2016/0175520 A1 | 6/2016 | Palerm et al. |
| 2016/0228641 A1 | 8/2016 | Gescheit et al. |
| 2016/0243318 A1 | 8/2016 | Despa et al. |
| 2016/0256087 A1* | 9/2016 | Doyle, III ............. A61B 5/725 |
| 2016/0302054 A1 | 10/2016 | Kimura et al. |
| 2016/0331310 A1 | 11/2016 | Kovatchev |
| 2016/0354543 A1 | 12/2016 | Cinar et al. |
| 2017/0049386 A1 | 2/2017 | Abraham et al. |
| 2017/0143900 A1 | 5/2017 | Rioux et al. |
| 2017/0173261 A1* | 6/2017 | O'Connor ............. G16H 40/63 |
| 2017/0189625 A1* | 7/2017 | Cirillo ................ A61M 5/3155 |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0348482 A1 | 12/2017 | Duke et al. |
| 2018/0036495 A1* | 2/2018 | Searle ................... A61M 5/482 |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | Ambrosio |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1* | 7/2018 | Edwards ................ G16H 40/67 |
| 2018/0289891 A1 | 10/2018 | Finan et al. |
| 2018/0296757 A1 | 10/2018 | Finan et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0240403 A1 | 8/2019 | Palerm et al. |
| 2019/0290844 A1 | 9/2019 | Monirabbasi et al. |
| 2019/0336683 A1 | 11/2019 | O'Connor et al. |
| 2019/0336684 A1 | 11/2019 | O'Connor et al. |
| 2019/0348157 A1 | 11/2019 | Booth et al. |
| 2020/0046268 A1 | 2/2020 | Patek et al. |
| 2020/0101222 A1 | 4/2020 | Lintereur et al. |
| 2020/0101223 A1* | 4/2020 | Lintereur ............... G16H 50/30 |
| 2020/0101225 A1 | 4/2020 | O'Connor et al. |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2022/0023536 A1 | 1/2022 | Graham et al. |

FOREIGN PATENT DOCUMENTS

| | | |
|---|---|---|
| DE | 19756872 A1 | 7/1999 |
| EP | 0341049 A2 | 11/1989 |
| EP | 0496305 A2 | 7/1992 |
| EP | 0549341 A1 | 6/1993 |
| EP | 1491144 A1 | 12/2004 |
| EP | 1571582 A2 | 9/2005 |
| EP | 0801578 B1 | 7/2006 |
| EP | 2666520 A1 | 10/2009 |
| EP | 2139382 A1 | 1/2010 |
| EP | 2397181 A1 | 12/2011 |
| EP | 2695573 A2 | 2/2014 |
| EP | 2830499 A1 | 2/2015 |
| EP | 2897071 B1 | 5/2019 |
| EP | 3607985 A1 | 2/2020 |

(56) References Cited

FOREIGN PATENT DOCUMENTS

| | | |
|---|---|---|
| GB | 2443261 A | 4/2008 |
| JP | 51125993 A | 11/1976 |
| JP | 02131777 A | 5/1990 |
| JP | 2004283378 A | 10/2004 |
| JP | 2017525451 A | 9/2017 |
| JP | 2018153569 A | 10/2018 |
| JP | 2019525276 A | 9/2019 |
| TW | 200740148 A | 10/2007 |
| TW | M452390 U | 5/2013 |
| WO | 9800193 A1 | 1/1998 |
| WO | 9956803 A1 | 11/1999 |
| WO | 0030705 A1 | 6/2000 |
| WO | 0032258 A1 | 6/2000 |
| WO | 0172354 A2 | 10/2001 |
| WO | 2002015954 A2 | 2/2002 |
| WO | 0243866 A2 | 6/2002 |
| WO | 02082990 A1 | 10/2002 |
| WO | 03016882 A1 | 2/2003 |
| WO | 03039362 A1 | 5/2003 |
| WO | 03045233 A1 | 6/2003 |
| WO | 2004043250 A1 | 5/2004 |
| WO | 04092715 A1 | 10/2004 |
| WO | 2005051170 A2 | 6/2005 |
| WO | 2005082436 A1 | 9/2005 |
| WO | 05110601 A1 | 11/2005 |
| WO | 2006053007 A2 | 5/2006 |
| WO | 2007064835 A2 | 6/2007 |
| WO | 2007078937 A1 | 7/2007 |
| WO | 2008024810 A2 | 2/2008 |
| WO | 2008029403 A1 | 3/2008 |
| WO | 2008133702 A1 | 11/2008 |
| WO | 2009045462 A1 | 4/2009 |
| WO | 2009049252 A1 | 4/2009 |
| WO | 2009066287 A3 | 5/2009 |
| WO | 2009066288 A1 | 5/2009 |
| WO | 2009098648 A2 | 8/2009 |
| WO | 2009134380 A2 | 11/2009 |
| WO | 2010053702 A1 | 5/2010 |
| WO | 2010132077 A1 | 11/2010 |
| WO | 2010138848 A1 | 12/2010 |
| WO | 2010147659 A2 | 12/2010 |
| WO | 2011095483 A1 | 8/2011 |
| WO | 2012045667 A2 | 4/2012 |
| WO | 2012108959 A1 | 8/2012 |
| WO | 2012134588 A1 | 10/2012 |
| WO | 2013078200 A1 | 5/2013 |
| WO | 2013134486 A2 | 9/2013 |
| WO | 20130149186 A1 | 10/2013 |
| WO | 2013177565 A1 | 11/2013 |
| WO | 2013182321 A1 | 12/2013 |
| WO | 2014194183 A2 | 12/2014 |
| WO | 2015056259 A1 | 4/2015 |
| WO | 2015081337 A2 | 6/2015 |
| WO | 2015187366 A1 | 12/2015 |
| WO | 2016004088 A1 | 1/2016 |
| WO | 2016041873 A1 | 3/2016 |
| WO | 2016089702 A1 | 6/2016 |
| WO | 2016141082 A1 | 9/2016 |
| WO | 2016161254 A1 | 10/2016 |
| WO | 2017091624 A1 | 6/2017 |
| WO | 2017105600 A1 | 6/2017 |
| WO | 2017184988 A1 | 10/2017 |
| WO | 2017205816 A1 | 11/2017 |
| WO | 2018009614 A1 | 1/2018 |
| WO | 2018067748 A1 | 4/2018 |
| WO | 2018120104 A1 | 7/2018 |
| WO | 2018136799 A1 | 7/2018 |
| WO | 2018204568 A1 | 11/2018 |
| WO | 2019077482 A1 | 4/2019 |
| WO | 2019094440 A1 | 5/2019 |
| WO | 2019213493 A1 | 11/2019 |
| WO | 2019246381 A1 | 12/2019 |
| WO | 2020081393 A1 | 4/2020 |
| WO | 2021011738 A1 | 1/2021 |

OTHER PUBLICATIONS

International Search Report and Written Opinion for the International Patent Application No. PCT/US2020/052125, dated Aug. 12, 2020, 15 pages.

International Search Report and Written Opinion for the International Patent Application No. PCT/US2020/050332, dated Sep. 12, 2020, 12 pages.

European Patent Office, "Notification of Transmittal of the ISR and the Written Opinion of the International Searching Authority, or the Declaration," in PCT Application No. PCT/GB2015/050248, dated Jun. 23, 2015, 12 pages.

International Search Report and Written Opinion for International Patent Application No. PCT/US2021/051027, dated Jan. 7, 2022, 16 pages.

International Search Report and Written Opinion for International Patent Application No. PCT/US2021/052372, dated Jan. 26, 2022, 15 pages.

International Search Report and Written Opinion for the International Patent Application No. PCT/US2021/046607, dated Jan. 31, 2022, 20 pages.

International Search Report and Written Opinion for the International Patent Application No. PCT/US2021/055745, dated Feb. 14, 2022, 13 pages.

European Search Report for the European Patent Application No. 21168591.2, dated Oct. 13, 2021, 4 pages.

International Search Report and Written Opinion for the International Patent Application No. PCT/US2021/041954, dated Oct. 25, 2021, 13 pages.

International Search Report and Written Opinion for the International Patent Application No. PCT/US2021/047771, dated Dec. 22, 2021, 11 pages.

International Search Report and Written Opinion for the International Patent Application No. PCT/US2021/052855, dated Dec. 22, 2021, 11 pages.

Unger, Jeff, et al., "Glucose Control in the Hospitalized Patient," Emerg. Med 36(9):12-18 (2004).

Glucommander FAQ downloaded from https://adaendo.com/GlucommanderFAQ.html on Mar. 16, 2009.

Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.

Letters to the Editor regarding "Glucose Control in Critically Ill Patients," N Engl J Med 361: 1, Jul. 2, 2009.

"Medtronic is Leading a Highly Attractive Growth Market," Jun. 2, 2009.

Davidson, Paul C., et al. "Glucommander: An Adaptive, Computer-Directed System for IV Insulin Shown to be Safe, Simple, and Effective in 120,618 Hours of Operation," Atlanta Diabetes Associates presentation Nov. 16, 2003.

Davidson, Paul C., et al. "Pumpmaster and Glucommander," presented at the MiniMed Symposium, Atlanta GA, Dec. 13, 2003.

Kanji S., et al. "Reliability of point-of-care testing for glucose measurement in critically ill adults," Critical Care Med, vol. 33, No. 12, pp. 2778-2785, 2005.

Krinsley James S., "Severe hypoglycemia in critically ill patients: Risk factors and outcomes," Critical Care Med, vol. 35, No. 10, pp. 1-6, 2007.

International Searching Authority, Invitation to Pay Additional Fees, International Application No. PCT/US2006/004929, dated Jul. 27, 2006.

Farkas et al. ""Single-Versus Triple-Lumen Central Catheter-Related Sepsis: A Prospective Randomized Study in a Critically Ill Population"" The American Journal of Medicine Sep. 1992vol. 93 p. 277-282.

Davidson, Paul C., et al., A computer-directed intravenous insulin system shown to be safe, simple,and effective in 120,618 h of operation. Diabetes Care, vol. 28, No. 10, Oct. 2005, pp. 2418-2423.

(56) References Cited

OTHER PUBLICATIONS

International Search Report and Written Opinion for the International Patent Application No. PCT/US2021/016283, dated Jun. 2, 2021, 15 pages.

Gorke, A. "Microbial contamination of haemodialysis catheter connections." EDTNA/ERCA journal (English ed.) vol. 31,2 (2005): 79-84. doi:10.1111/j.1755-6686.2005.tb00399.x.

Lovich et al. "Central venous catheter infusions: A laboratory model shows large differences in drug delivery dynamics related to catheter dead volume" Critical Care Med 2007 vol. 35, No. 12.

Van Den Berghe, Greet, M.D., Ph.D., et al., Intensive Insulin Therapy in Critically III Patients, The New England Journal of Medicine, vol. 345, No. 19, Nov. 8, 2001, pp. 1359-1367.

Templeton et al., "Multilumen Central Venous Catheters Increase Risk for Catheter-Related Bloodstream Infection: Prospective Surveillance Study" Infection 2008; 36: 322-327.

Wilson, George S., et al., Progress toward the Development of an Implantable Sensor for Glucose, Clin. Chem., vol. 38, No. 9, 1992, pp. 1613-1617.

Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.

International Search Report and Written Opinion, International Application No. PCT/US2010/033794 dated Jul. 16, 2010.

International Search Report and Written Opinion in PCT/US2008/079641 dated Feb. 25, 2009.

Berger, ""Measurement of Analytes in Human Serum and Whole Blood Samples by Near-Infrared Raman Spectroscopy,"" Ph.D. Thesis, Massachusetts Institute of Technology, Chapter 4, pp. 50-73, 1998.

Berger, "An Enhanced Algorithm for Linear Multivariate Calibration," Analytical Chemistry, vol. 70, No. 3, pp. 623-627, Feb. 1, 1998.

Billman et al., "Clinical Performance of an In line Ex-Vivo Point of Care Monitor: A Multicenter Study," Clinical Chemistry 48: 11, pp. 2030-2043, 2002.

Widness et al., "Clinical Performance on an In-Line Point-of-Care Monitor in Neonates"; Pediatrics, vol. 106, No. 3, pp. 497-504, Sep. 2000.

Finkielman et al., "Agreement Between Bedside Blood and Plasma Glucose Measurement in the ICU Setting" retrieved from http://www.chestjournal.org; CHEST/127/5/May 2005.

Glucon Critical Care Blood Glucose Monitor; Glucon; retrieved from http://www.glucon.com.

Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.

Vonach et al., "Application of Mid-Infrared Transmission Spectrometry to the Direct Determination of Glucose in Whole Blood," Applied Spectroscopy, vol. 52, No. 6, 1998, pp. 820-822.

Muniyappa et al., "Current Approaches for assessing insulin sensitivity and resistance in vivo: advantages, limitations, and appropriate usage," AJP-Endocrinol Metab, vol. 294, E15-E26, first published Oct. 23, 2007.

R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2000.

International Preliminary Report on Patentability for the International Patent Application No. PCT/US2019/053603, dated Apr. 8, 2021, 9 pages.

International Search Report and Written Opinion for the International Patent Application No. PCT/US2019/053603, dated Jan. 7, 2020, 16 pages.

Dassau et al., "Detection of a meal using continuous glucose monitoring: Implications for an artificial [beta]-cell." Diabetes Care, American Diabetes Association, Alexandria, VA, US, 31(2):295-300 (2008).

Cameron et al., "Probabilistic Evolving Meal Detection and Estimation of Meal Total Glucose Appearance Author Affiliations", J Diabetes Sci and Tech.Vol., Diabetes Technology Society ;(5):1022-1030 (2009).

Lee et al., "A closed-loop artificial pancreas based on model predictive control: Human-friendly identification and automatic meal disturbance rejection", Biomedical Signal Processing and Control, Elsevier, Amsterdam, NL, 4 (4):1746-8094 (2009).

International Search Report and Written Opinion for the InternationalPatent Application No. PCT/US2021/018297, dated May 18, 2021, 18 pages.

An Emilia Fushimi: "Artificial Pancreas: Evaluating the ARG Algorithm Without Meal Announcement", Journal of Diabetes Science and Technology Diabetes Technology Society, Mar. 22, 2019, pp. 1025-1043.

International Search Report and Written Opinion for the International Patent Application No. PCT/US2021/017441, dated May 25, 2021, 12 pages.

International Search Report and Written Opinion for the InternationalPatent Application No. PCT/US2021/017664, dated May 26, 2021, 16 pages.

Mirko Messori et al: "Individualized model predictive control for the artificial pancreas: In silico evaluation of closed-loop glucose control", IEEE Control Systems, vol. 38, No. 1, Feb. 1, 2018, pp. 86-104.

International Search Report and Written Opinion for the International Patent Application No. PCT/US2021/017662, dated May 26, 2021, 14 pages.

Anonymous: "Reservoir Best Practice and Top Tips" Feb. 7, 2016, URL: https://www.medtronic-diabetes.co.uk/blog/reservoir-best-practice-and-top-tips, p. 1.

Gildon Bradford: "InPen Smart Insulin Pen System: Product Review and User Experience" Diabetes Spectrum, vol. 31, No. 4, Nov. 15, 2018, pp. 354-358.

International Search Report and Written Opinion for the International Patent Application No. PCT/US2021/016050, dated May 27, 2021, 16 pages.

International Search Report and Written Opinion for the International Patent Application No. PCT/US2020/065226, dated May 31, 2021, 18 pages.

International Search Report and Written Opinion for the International Patent Application No. PCT/US2021/017659, dated May 31, 2021, 13 pages.

Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Jul. 2020, pp. 2064-2072.

Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.

Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.

Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.

E. Atlas et al., "MD-Logic Artificial Pancreas System: A pilot study in adults with type 1 diabetes", Diabetes Care, vol. 33, No. 5, Feb. 11, 2010, pp. 1071-1076.

Anonymous: "Fuzzy control system", Wikipedia, Jan. 10, 2020. URL: https://en.wikipedia.org/wlindex.php?title=Fuzzy_control_system&oldid=935091190 Retrieved: May 25, 2021.

International Search Report and Written Opinion for the International Patent Application No. PCT/US2021/022694, dated Jun. 25, 2021, 13 pages.

International Search Report and Written Opinion for the Application No. PCT/US2017/015601, dated May 16, 2017, 12 pages.

International Search Report and Written Opinion for the Application No. PCT/US2018/018901, dated Aug. 6, 2018, 12 pages.

International Search Report and Written Opinion for Application No. PCT/US2018/052467, dated Jan. 4, 2019, 13 pages.

(56) References Cited

OTHER PUBLICATIONS

"How to Create a QR Code that Deep Links to Your Mobile App", Pure Oxygen Labs, web<https://pureoxygenlabs.com/how-to-create-a-qr-codes-that-deep-link-to-your-mobile-app/>. Year:2017.

"Read NFC Tags with an iPHone App on iOS 11", GoToTags, Sep. 11, 2017, web <https://gototags.com/blog/read-nfc-tags-with-an-iphone-app-on-ios-11/>. (Year:2017).

International Search Report and Written Opinion for International Application No. PCT/US2016/063350, dated Mar. 27, 2017, 9 pages.

PCT International Search Report and Written Opinion dated Apr. 29, 2015, received in corresponding PCT Application No. PCT/US16/18452, 9 pages.

International Preliminary Report on Patentability dated Aug. 31, 2017, issued in PCT Patent Application No. PCT/US2016/018452, 7 pages.

International Search Report and Written Opinion for the International Patent Application No. PCT/US2022/013470, dated May 6, 2022, 14 pages.

International Search Report and Written Opinion for the International Patent Application No. PCT/US2022/013473, dated May 6, 2022, 13 pages.

International Search Report and Written Opinion for the International Patent Application No. PCT/US2022/019079, dated Jun. 2, 2022, 14 pages.

International Search Report and Written Opinion for the International Patent Application No. PCT/US2022/018453, dated Jun. 2, 2022, 13 pages.

International Search Report and Written Opinion for the International Patent Application No. PCT/US22/018700, dated Jun. 7, 2022, 13 pages.

International Search Report and Written Opinion for the International Patent Application No. PCT/US22/019080, dated Jun. 7, 2022, 14 pages.

International Search Report and Written Opinion for the International Patent Application No. PCT/US22/019664, dated Jun. 7, 2022, 14 pages.

Herrero Pau et al: "Enhancing automatic closed-loop glucose control in type 1 diabetes with an adaptive meal bolus calculator-in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.

Herrero Pau Ei Al: "Enhancing automatic closed-loop glucose control in type 1 diabetes with an adaptive meal polus calculator-in silicoevaluation under intra-day variability", Computer Methods and Programs in Biomedicine, Elsevier, Amsterdam, Nl, vol. 146, Jun. 1, 2017 (2017-06-01), pp. 125-131, XP085115607, Ssn: 0169-2607, D0l:10.1016/J.CMPB.2017.05.010.

Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, p. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand col. line 16- line 23.

Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kemnel_density_estimation&oldid=988508333 [retrieved on Jun. 6, 2022].

Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.

Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].

Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/issues/2473 [retrieved on Jun. 6, 2022].

Medication Bar Code System Implementation Planning Section I: A Bar Code Primer for Leaders, Aug. 2013.

Medication Bar Code System Implementation Planning Section II: Building the Case for Automated Identification of Medications, Aug. 2013.

Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.

Fox, Ian G.; Machine Learning for Physiological Time Series: Representing and Controlling Blood Glucose for Diabetes Management; University of Michigan. ProQuest Dissertations Publishing, 2020. 28240142. (Year: 2020).

International Search Report and Written Opinion for the International Patent Application No. PCT/US2022/012896, dated Apr. 22, 2022, 15 pages.

* cited by examiner

FLUID DELIVERY DEVICE WITH SENSOR

CROSS-REFERENCE TO RELATED APPLICATIONS

This application is a continuation of U.S. application Ser. No. 15/714,496, filed Sep. 25, 2017, which claims the benefit of U.S. Provisional Application No. 62/398,792, filed Sep. 23, 2016, which are incorporated herein by reference in their entirety.

TECHNICAL FIELD

Embodiments generally relate to medication delivery. More particularly, embodiments relate to wearable drug delivery devices configured to monitor medication flow.

BACKGROUND

Drug delivery devices (e.g., infusion devices or pumps) can experience conditions that can lead to under-delivery or over-delivery of an infusate into a patient. For example, blockages in a fluid path (e.g., as caused by an occlusion) can cause a backup of fluid within the pump and a subsequent increase in fluid path pressure. When a blockage clears, the pressurized infusate can be delivered in a single bolus in an undesirable or unintended manner.

When air is trapped in the fluid path, changes in atmospheric pressure can cause the trapped air to expand or compress and to displace (e.g., by suction) fluid into or out of the patient. These situations can also cause under-delivery or under-delivery of the infusate into the patient. Swimming or flying are examples of common activities engaged in by a patient that can result in under-delivery and over-delivery without the patient's knowledge.

Additionally, when air is trapped in the fluid path, changes in ambient temperature can also cause the trapped air to expand or compress and to displace fluid into or out of the patient. Similarly, these situations can also cause under-delivery or over-delivery of the infusate into the patient. Swimming in the ocean or swimming in an unheated pool or using a heated blanket are examples of common activities engaged in by a patient that can result in under-delivery and over-delivery of the infusate without a patient's knowledge.

Many conventional drug delivery devices including infusion devices or pumps detect occlusions by monitoring the time it takes for the pump to actuate. This conventional approach can produce erroneous results based on variabilities within the drive system (e.g., due to friction, power sagging, mechanical variability of parts, etc.).

Even conventional systems that directly measure the pressure within the pump fluid path often do not detect changes in atmospheric pressure which can lead to over-delivery and under-delivery. These conventional systems typically utilize pressure sensors which measure pressure relative to atmospheric pressure and are incapable of detecting any change in atmospheric pressure which can lead to over-delivery and under-delivery without a patient's knowledge as described above.

Accordingly, what is needed is a drug delivery device with improved capabilities for detecting under-delivery and over-delivery conditions during intended delivery periods or unintended delivery periods that can be caused by a variety of factors including changes in atmospheric pressure.

DETAILED DESCRIPTION

Figure 1:
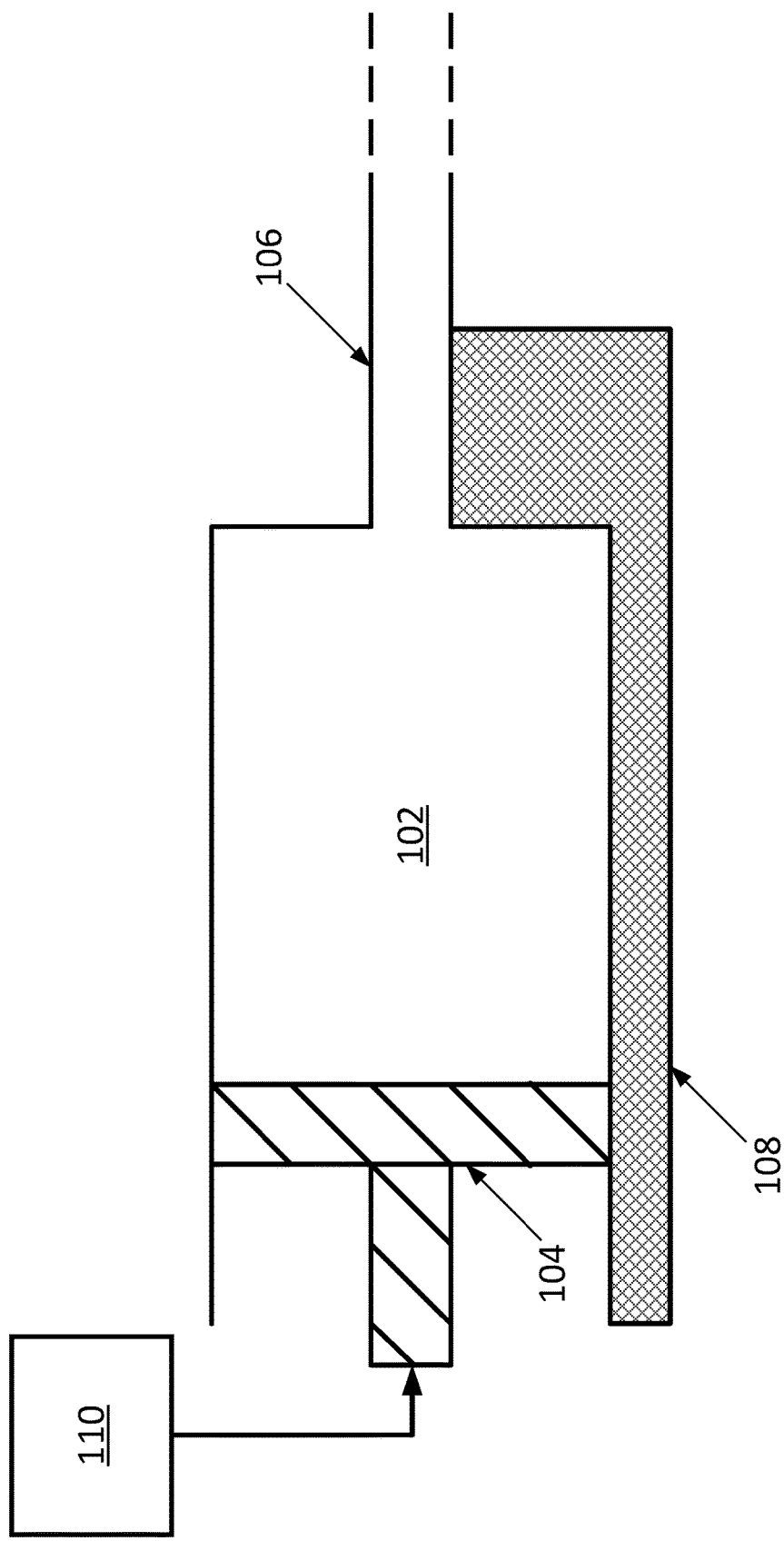
FIG. 1 illustrates a first exemplary pump system.

This disclosure presents various systems, components, and methods related to a drug delivery device. Each of the systems, components, and methods disclosed herein provides one or more advantages over conventional systems, components, and methods.

Various embodiments include a wearable drug delivery device having a pump system. The pump system can be used to deliver a stored liquid drug or other therapeutic agent to a user or patient. An absolute pressure sensor can be positioned within the fluid path of the drug delivery device and/or pump system. The absolute pressor sensor can detect both ambient pressure (e.g., absolute or atmospheric pressure) and relative pressure (gage or pumping pressure). Based on the detected pressures, the effects of external ambient pressure on air with the pump system and/or fluid path can be determined during intended drug delivery events and unintended drug delivery events. In turn, under-delivery and/or over-delivery of the liquid drug can be determined. Based on the severity of the determined under-delivery or over-delivery of the liquid drug, alarms of different urgencies can be provided to the user. Other embodiments are disclosed and described including various embodiments directed to the use of a flow sensor to detect the aforementioned over-delivery and under-delivery conditions.

Various embodiments provide techniques for monitoring the absolute and relative pressures associated with a liquid drug pump system of a wearable drug delivery device. Based on the monitored pressures, an amount (e.g., corresponding to an over-delivery or an under-delivery) and direction (e.g., into or out of the pump system) of unintended liquid drug flow can be determined. If the amount of the unintended liquid drug exceeds one or more thresholds, one or more associated alarms can be provided to a user. Monitoring can be provided during intended drug delivery operations when the pump system is directed to provide the liquid drug to the user and during unintended drug delivery operations when the pump system is directed to not provide the liquid drug to the user. Other embodiments are disclosed and described.

The pressure sensor 202 can be an absolute pressure sensor that can detect both ambient pressure (e.g., absolute or atmospheric pressure) and relative pressure (e.g., gage or pumping pressure) introduced as the pump system 200 displaces fluid (e.g., the infusate stored in the reservoir 102) in the overall fluid path of the pump system (e.g., including the reservoir 102 and the fluid path component 106). By using an absolute pressure sensor as the pressure sensor 202, it is possible to measure the effects of external ambient pressure on air within the reservoir 102. Further, by using an absolute pressure sensor as the pressure sensor 202, it is possible to measure the effects of the internal pumping pressure changes due to pumping (e.g., expelling the infusate from the reservoir 102 for delivery to the patient). By measuring these effects, the pump system 200 can detect situations of possible over-delivery and/or under-delivery of the infusate to the patient due to both intended and unintended actions (e.g., during periods of intended delivery and periods of unintended delivery). Further, the pump system 200 can provide indications of such over-delivery and/or under-delivery conditions or situations to the patient, allowing the patient to respond accordingly.

FIG. 1 illustrates a pump system that can be used to deliver an infusate to a patient. The pump system can include a reservoir 102, a plunger 104, a fluid path component 106, a supporting mechanical structure or component 108, and a plunger or pump drive mechanism 110. The reservoir 102 can store or hold the infusate. The infusate can be any liquid drug and/or therapeutic agent. The plunger 104 can be used to expel the infusate from the reservoir 102 for delivery to a patient or user. The reservoir 102 can be coupled to the fluid path component 106. The fluid path component 106 can be coupled to the patient.

The supporting mechanical structure 108 can provide structural support to the reservoir 102, the fluid path component 106, and/or the plunger drive mechanism 110. The supporting mechanical structure 108 is not limited to the presentation depicted in FIG. 1. The supporting mechanical structure 108 can encase, surround, or otherwise provide structural support for the reservoir 102, the fluid path component 106, and/or the plunger drive mechanism 110. The plunger drive mechanism 110 can be any mechanical or electromechanical system that can advance the plunger 104 into the reservoir 102. As the plunger drive mechanism 110 is operated and the plunger 104 advances into the reservoir, the infusate can be expelled from the reservoir 102 and provided to the patient by way of the fluid path component 104. The fluid path component 106 can include or can be coupled to a needle or cannula providing access (e.g., via an outlet) to the patient.

The pump system shown in FIG. 1 can be part of a drug delivery device. As an example, the pump system can be part of a wearable drug delivery device. In various embodiments, the pump system can be used to deliver insulin to a patient. The pump system can be considered to be an infusion pump system. The overall fluid path of the pump system shown in FIG. 1 can include the reservoir 102 as well as the fluid path component 106 that couples the reservoir 102 to the patient.

During periods of operation—for example, when the pump system of FIG. 1 is specifically directed to deliver a portion of the infusate to the patient—the pump system can erroneously over-deliver or under-deliver a desired amount of infusate to the patient. Under-delivery and over-delivery can be caused by a variety of factors including changes in atmospheric pressure, changes in ambient temperature, and occlusions in the fluid path. Further, during periods of unintended delivery—for example, when the pump system of FIG. 1 is specifically directed not to deliver any infusate to the patient—these factors can still cause delivery of unintended amounts of the infusate to the patient (or backflow of the infusate).

The pump system shown in FIG. 1 does not include any capability to detect and monitor any over-delivery or under-delivery of the infusate during intended delivery periods or unintended delivery periods. The pump system of FIG. 1 is further unable to account for any such under or over-delivery condition and is incapable of notifying the patient as to any under or over-delivery condition. Consequently, operation of the pump system of FIG. 1 can be inefficient and even hazardous to the patient.

Figure 2:
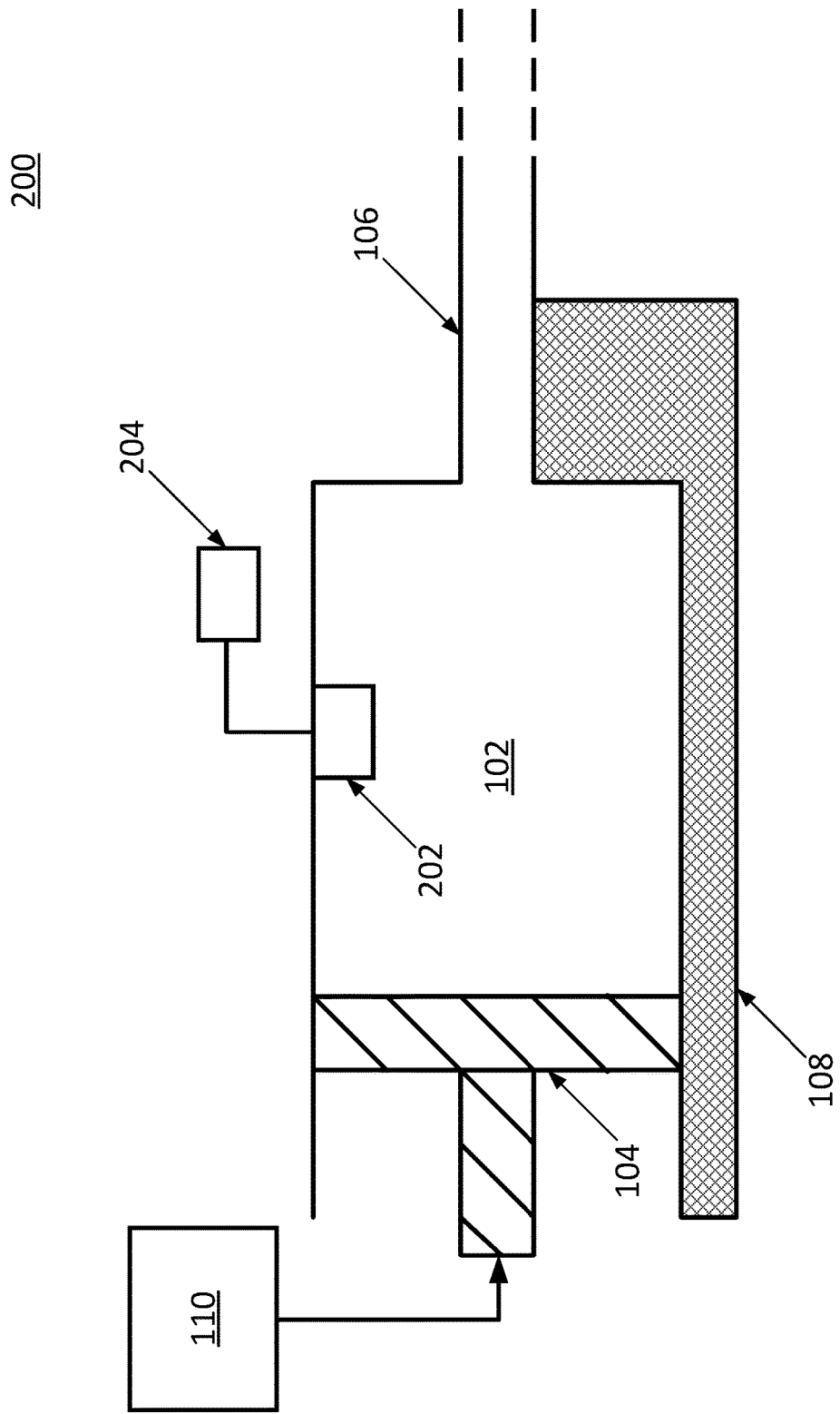
FIG. 2 illustrates a second exemplary pump system incorporating a pressure sensor.

FIG. 2 illustrates a pump system 200 (or infusion pump system 200) for providing monitoring of any over-delivery or under-delivery condition during any intended or unintended drug delivery. As shown in FIG. 2, the pump system 200 can include the reservoir 102, the plunger 104, the fluid path component 106, the supporting component 108, and the plunger drive mechanism 110. The pump system 200 can further include a pressure sensor 202 and a monitoring component 204. The pump system 200 can, among other features, detect flow (e.g., unintended flow) of the infusate through pressure sensing as described herein.

The pressure sensor 202 can be an absolute pressure sensor that can detect both ambient pressure (e.g., absolute or atmospheric pressure) and relative pressure (e.g., gage or pumping pressure) introduced as the pump system 200 displaces fluid (e.g., the infusate stored in the reservoir 102) in the overall fluid path of the pump system (e.g., including the reservoir 102 and the fluid path component 106). By using an absolute pressure sensor as the pressure sensor 202, it is possible to measure the effects of external ambient pressure on air within the reservoir 102. Further, by using an absolute pressure sensor as the pressure sensor 202, it is possible to measure the effects of the internal pumping pressure changes due to pumping (e.g., expelling the infusate from the reservoir 102 for delivery to the patient). By measuring these effects, the pump system 200 can detect situations of possible over-delivery and/or under-delivery of the infusate to the patient due to both intended and unintended actions (e.g., during periods of intended delivery and periods of unintended delivery). Further, the pump system 200 can provide indications of such over-delivery and/or under-delivery conditions or situations to the patient, allowing the patient to respond accordingly. This enables a drug delivery device that incorporates the pump system 200 to operate more effectively and safely and to provide an improved experience for the patient.

In various embodiments, the pressure sensor 202 can be integrated into the reservoir 102 as shown in FIG. 2. In various embodiments, the pressure sensor 202 can be integrated anywhere along the overall fluid path of the pump system 200 (e.g., including the reservoir 102 and/or the fluid path component 106) that is at the same approximate pressure as the outlet into the patient. An intervening membrane (not shown in FIG. 2 for simplicity) can be used to isolate the pressure sensor 202 from the infusate within the reservoir 102 and/or fluid path component 106. Alternatively, a pliable gel or sufficiently soft rubber can be used to isolate the pressure sensor 202 from the infusate.

In various embodiments, the pressure sensor 202 can have a round body to simplify sealing against the reservoir 102 and/or the fluid path component 106. In various embodiments, an integral lip seal can be used to seal the interface between the body of the pressure sensor 202 and the reservoir 102 and/or fluid path component 106.

The pressure sensor 202 can be coupled to a monitoring component 204. The pressure sensor 202 can measure the absolute pressure of the reservoir 102 and/or the fluid path component 106 (e.g., the overall fluid path of the pump system 200) and can provide an output signal to the monitoring component 204. In various embodiments, the pressure sensor 202 can take continuous readings of the absolute pressure. The output signal from the pressure sensor 202 can indicate the measured or detected absolute pressure and/or any other measured, detected, or derived pressure value.

The monitoring component 204 can process the received signal from the pressure sensor 202. The monitoring component 204 can be implemented in hardware, software, or any combination thereof. In various embodiments, the monitoring component 204 can be implemented using a processor and associated memory and can execute one or more monitoring algorithms or processes as described herein. In various embodiments, the monitoring component 204 can be implemented as dedicated hardware (e.g., as an application specific integrated circuit (ASIC)). The monitoring component 204 can be a constituent part of the pump system 200, can be implemented in software as a computational model, or can be implemented external to the pump system 200 (e.g., remotely).

In various embodiment, the output signal generated by the pressure sensor 202 can be a voltage signal, a current signal, and/or an electrical charge signal. In various embodiment, the output signal generated by the pressure sensor can be a data signal (e.g., an analog or digital data signal) such as, for example, an inter-integrated circuit (I2C), serial peripheral interface (SPI), or any other known or customized synchronous or asynchronous data communication stream. In general, the output signal from the pressure sensor 202 can indicate a measured pressure. Further, the pressure sensor 202 and the monitoring component 204 can communicate over any known signaling protocol or standard including any known wired or wireless communication or signaling protocol. In various embodiments, the signal generated by the pressure sensor 202 for output and delivery to the monitoring component can be temperature compensated to remove or mitigate any error due to temperature changes. The monitoring component 204 can convert the signal received from the pressure sensor 202 into an indication of absolute pressure (e.g., pounds per square inch absolute (psia)).

The monitoring component 204 can generate a characterization of the fluid capacitance of the reservoir 102 and/or the fluid path component 106 (e.g., a model of the fluid capacitance of the overall fluid path of the pump system 200). Alternatively, the monitoring component 204 can be provided such information. For example, the monitoring component 204 can include a memory component or can access a memory component storing such information. In various embodiments, one or more components (e.g., external hardware components) can be used to generate characterizations of the fluid path fluid capacitance that can be provided to the monitoring component 204 in the form of data that can be stored, or integrally included as part of operational software. The characteristic fluid capacitance can be an input into a detection algorithm or monitoring process implemented by the monitoring component 204. The fluid capacitance can be considered to be the relationship between an internal pressure of the reservoir 102 and/or the fluid path component 106 (e.g., the overall fluid path of the pump system 200) and the volume of fluid necessary to achieve the specific pressure.

As will be appreciated by a person of ordinary skill in the art, the nature of fluid capacitance is roughly equivalent to electrical capacitance in which the infusate acts as electrical charge, internal gage pressure behaves as the positive voltage in an electrical circuit, the hydraulic stiffness of a fluid path acts as the electrical capacitance of a capacitor, and the fluid path outlet flow restriction acts as a resistor does in the electrical equivalent. Additionally, counter infusion pressure provided by the patient at the infusion site acts as the ground potential. Further, when counter-infusion pressure matches the infusion pressure, flow (e.g., to the patient) stops. If counter-infusion pressure exceeds internal gage pressure, counter flow (flow into the fluid path of the pump system 200 and away from the patient) can occur.

The fluid capacitance can be characterized using a numeric value, or a range of numeric values, or a variable model which defines the characteristic fluid capacitance of the overall fluid path of the pump system 200. In various embodiments, a memory associated with the monitoring component 204 can store values for characterizing the fluid capacitance associated with the pump system 200. In various embodiments, the one or more stored values can be based on characterization of the specific design of the pump system 200.

As the pump system 200 operates to expel the infusate from the reservoir 102 and into the fluid path component 106 for delivery to the patient, the fluid capacitance associated with the pump system 200 can change. For example, the fluid capacitance can change based on changes to the effective stiffness of the reservoir 102 as the plunger 104 is advanced further into the reservoir 102 by the plunger drive mechanism 110. As another example, changes in the stiffness of the supporting mechanical structure 108, the pump drive mechanism 110, or the interfaces between these components can cause the fluid capacitance to change. Accordingly, the monitoring component 204 can include a range of characterized fluid capacitance values that account for any such change. In various embodiments, the monitoring component 204 can be configured to use a function or other mathematical model capable of defining the change in fluid capacitance over the range of operation of the pump system 200—for example, from fully filled to empty. Based on an indication of the fluid capacitance—for example, by generating an estimate of the fluid capacitance over time as the pump system 200 operates—the monitoring component 204 can detect and determine, for example, any under-delivered fluid based on an indication of pressure provided by the pressure sensor 202.

By monitoring the absolute pressure within the fluid path of the pump system 200, the amount and direction of flow from the fluid path of the pump system 200 can be determined by the monitoring component 204. Based on determined changes in the pressure of the fluid path of the pump system 200, and the characteristic fluid capacitance of the fluid path of the pump system 200, a total net flow of fluid (e.g., the infusate) from a first point in time to a later, second point in time can be determined. Based on the amount and direction of flow error over time (e.g., unintended or undesired flow of the infusate into or out of the fluid path of the pump system 200), the monitoring component 204 can determine if an alert or other alarm should be issued to the patient.

During operation of the pump system 200, as the plunger 104 advances further into the reservoir 102, the fluid capacitance associated with the pump system 200 can change and the pressure associated with the pump system 200 can also change. The monitoring component 204, by monitoring the pressure and fluid capacitance of the pump system 200 over time, can determine net fluid flow over time—either intended or unintended and either into or out of the pump system 200 (or a drug delivery device in which the pump system 200 can be included). In various embodiments, to estimate an amount of fluid flow, the monitoring component 200 can estimate an amount of undelivered volume of fluid (e.g., the infusate within the fluid path or reservoir 102) at two different points in time.

Accordingly, based on data or information provided by the pressure sensor 202, the monitoring component 204 can monitor an amount of infusate delivered over time to determine if the amount is a proper or correct amount based on a predetermined level of intended infusate delivery. The monitoring component 204 can further determine if changes in physical conditions or the environment in which the pump system 200 operates can lead to under-delivery or over-delivery of the infusate during periods of delivery or non-delivery. The flow direction and the amount of fluid as determined by the monitoring component 204 can be compared to one or more operational thresholds, to determine if an alert should be issued to the patient. This allows the patient to more safely use the pump system 200 and to take corrective action if necessary.

In various embodiments, the pump system 200 and/or the monitoring component 204 can operate to monitor the following operational conditions (e.g., errors) associated with the pump system:
1. Deviation in total infusate delivered (e.g., from a desired level of infusate to be delivered) during an intended delivery period/delivery operation;
2. Deviation in total infusate delivered over time from unintended delivery/non-intended delivery operation; and Further, in various embodiments, the pump system 200 and/or the monitoring component 204 (and/or a drug delivery device of which the pump system 200 can be a component) can operate to provide the following alarms as necessary based on monitoring flow direction and amount of flow:
1. Under-delivery of the infusate during pumping—can be caused by, for example, a partial occlusion in the fluid path of the pump system 200, increased back pressure, and/or decreased site viability;
2. No delivery of the infusate during pumping—can be caused by, for example, a full occlusion in the fluid path of the pump system 200 and an alarm can alert the patient to immediately replace the drug delivery device in which the pump system 200 operates;
3. Potential back-flow into pump system 200 delaying delivery—can be caused by, for example, ambient pressure changes from low pressure to high pressure (e.g., during landing in a flight); and
4. Potential out-flow from pump system 200 without pumping—can be caused by, for example, ambient pressure changes from high pressure to low pressure (e.g., during take-off in a flight).

For the first source of error listed above (i.e., deviation of total infusate delivered over time from intended delivery), the monitoring component 204 can monitor (e.g., continuously) the pressure in the fluid path of the pump system 200 from the start of an intended delivery event until the end of the intended delivery event during which, for example, a predetermined or desired amount of infusate is to be delivered. The monitoring component 204 can then compare the difference in the determined pressures (or the volume of undelivered fluid) to predetermined delivery thresholds. If the amount of infusate delivered is more than desired or intended, and exceeds a first threshold, then an alert or alarm can be provided to the user. If the amount of infusate delivered is less than desired or intended, and is less than a second threshold, then an alert or alarm can similarly be provided to the user. In this way, a patient can be made aware of under-delivery or over-delivery situations through pressure monitoring that enables flow amounts and directions to be determined.

In various embodiments, the alerts or alarms can be visual and/or audible and can include haptic and/or tactile feedback such as vibrational movement of the drug delivery device. Further, in various embodiments, the alarms can vary based on the type of alarm—for example, a first type of visual and/or audible alert for an over-delivery condition and a second, different visual and/or audible alert for an under-delivery condition. If the over or under-delivery condition stays within the set thresholds, then an alarm may not be provided (e.g., if the deviation from a desired delivery is minimal). Further, multiple thresholds can be established and compared such that more significant deviations from an intended delivery can trigger heightened alarm signals or indications or the patient.

In various embodiments, the thresholds can be dynamically adjusted. For example, the thresholds for comparison can be adjusted based on a de-rating factor that can be based on the total delivered amount of infusate and/or the current unmetabolized excess infusate remaining in the blood stream in the event of an over-delivery event. In various embodiments, the monitoring component 204 can determine an estimate of infusate yet to be delivered in the event of under-delivery by monitoring the capacity of fluid path pressure differential from the start of infusion.

In various embodiments, the monitoring component 204 can distinguish changes in pressure due to ambient (atmospheric) pressure changes from intended pumping pressure changes. In various embodiments, the monitoring component 204 can implement various filtering techniques including, for example, Bayesian nonlinear filters such as Kalman and/or particle filters to isolate and then compensate for random wandering pressure changes due to, for example, changing weather conditions. The monitoring component 204 can also employ band pass filtering to isolate pulsatile pumping pressure changes.

Atmospheric pressure can change with geographic location (e.g., altitude) as well as weather. Accordingly, the monitoring component 204 can include a rolling window filter for establishing or re-establishing a baseline atmospheric pressure. This baseline atmospheric pressure level can be used for comparison over any time period. In various embodiments, the baseline filter window implemented by the monitoring component 204 can be linked to the metabolization rate of the infusate when known which can be provided to the monitoring component 204.

As described above, the monitoring component 204 can include one or more thresholds and associated alarms that can be issued to a user. Further, as described above, multiple threshold levels and heightened alerts can be used for comparison to indicate an escalating intensity of alarm based on the degree of risk associated with any particular threshold being exceeded or not met—for example, based on the level of infusate delivery missed or the level of excessive infusate delivery.

In various embodiments, in the case of little to no delivery (e.g., due to an occlusion), thresholds can be set based on the specific risk of the infusate via a table of values stored in a memory (e.g., ROM and/or RAM memory or any other memory or look-up table) associated with the monitoring component 204

For the second source of error listed above (i.e., deviation of total infusate delivered over time from unintended delivery), the following can be contributing sources for any such deviation or error:
1. Expansion or contraction of air within the fluid path of the pump system 200 due to ambient pressure or temperature changes;

2. Physical compression of the fluid path of the pump system 200;
3. Unintended operation of the plunger 104 and/or pumping mechanism of the pump system 200;
4. Mechanical errors (e.g., incorrect drive train multiplier, thread errors, or cam errors); and
5. Siphoning due to air leaks in the fluid path of the pump system 200.

In various embodiments, the monitoring component 204 can monitor (e.g., sample) the pressure of the fluid path of the pump system 200 continuously (or semi-continuously to conserve power) during periods of intended non-delivery—that is, during times when the pump system 200 is not being directed to specifically provide the infusate to the patient. During these periods, the internal pressure of the fluid path of the pump system 200 is unlikely to change by more than an expected amount due to the narrow range of atmospheric pressure changes. By monitoring the fluid path pressure of the pump system 200, the monitoring component 204 can determine if any such changes in pressure are significant.

In situations where the atmospheric pressure can change by an amount more than an expected amount due to normal weather based atmospheric pressure (e.g., during flying on a commercial flight), the monitoring component 204 can determine the potential unintended delivery due to air expansion in the reservoir 104 and can alert the user to any potential risk associated with such determined unintended delivery. Additionally, the monitoring component 204 can alert the user of the opposite condition (e.g., back flow) that may occur following an increase in absolute pressure as would be experienced during normalization of aircraft cabin pressure upon landing during a flight.

Further, in situations where the atmospheric pressure can change by an amount more than an expected amount due to normal weather based atmospheric changes, but at a rate which is lower than typical air travel pressure changes (e.g., traversing altitude slowly as can happen when driving from a lower altitude to a higher altitude), the monitoring component 204 can determine the rate of change of atmospheric pressure. The monitoring component 204 can use this determined rate to properly adjust the intensity of alerts and/or alarms provided to the patient.

Overall, the monitoring component 204 can monitor pressure changes during periods of non-delivery (e.g., intended non-delivery) to determine if any fluid is unintentionally provided to the patient or being removed from the fluid path coupled to the patient. If the levels of unintended delivery exceed one or more thresholds during such periods, one or more associated alarms (e.g., of heightened intensity) can be provided to the user.

In various embodiments, the monitoring component 204 can use a rolling window low pass filter matched to the in vivo decay rate of the infusate within the patient's body, or based on a reasonable threshold which can be set by the user. Additional filtering techniques can be employed in other embodiments utilizing Kalman, particle, or non-linear filtering techniques.

In various embodiments, the pump system 200 can include a temperature sensor to alter the sampling frequency in response to the potential for expansion or contraction of air bubbles in the fluid path of the pump system 200. For example, if greater temperature swings are to be expected within the environment in which the pump system 200 operates, larger pressure swings may be expected to occur. Accordingly, monitoring and/or sampling of the pressure may be adjusted during such time periods to increase monitoring or sampling. The temperature sensor can be part of or can be coupled to the monitoring component 204 to provide a measure of temperature to the monitoring component 204.

Figure 3:
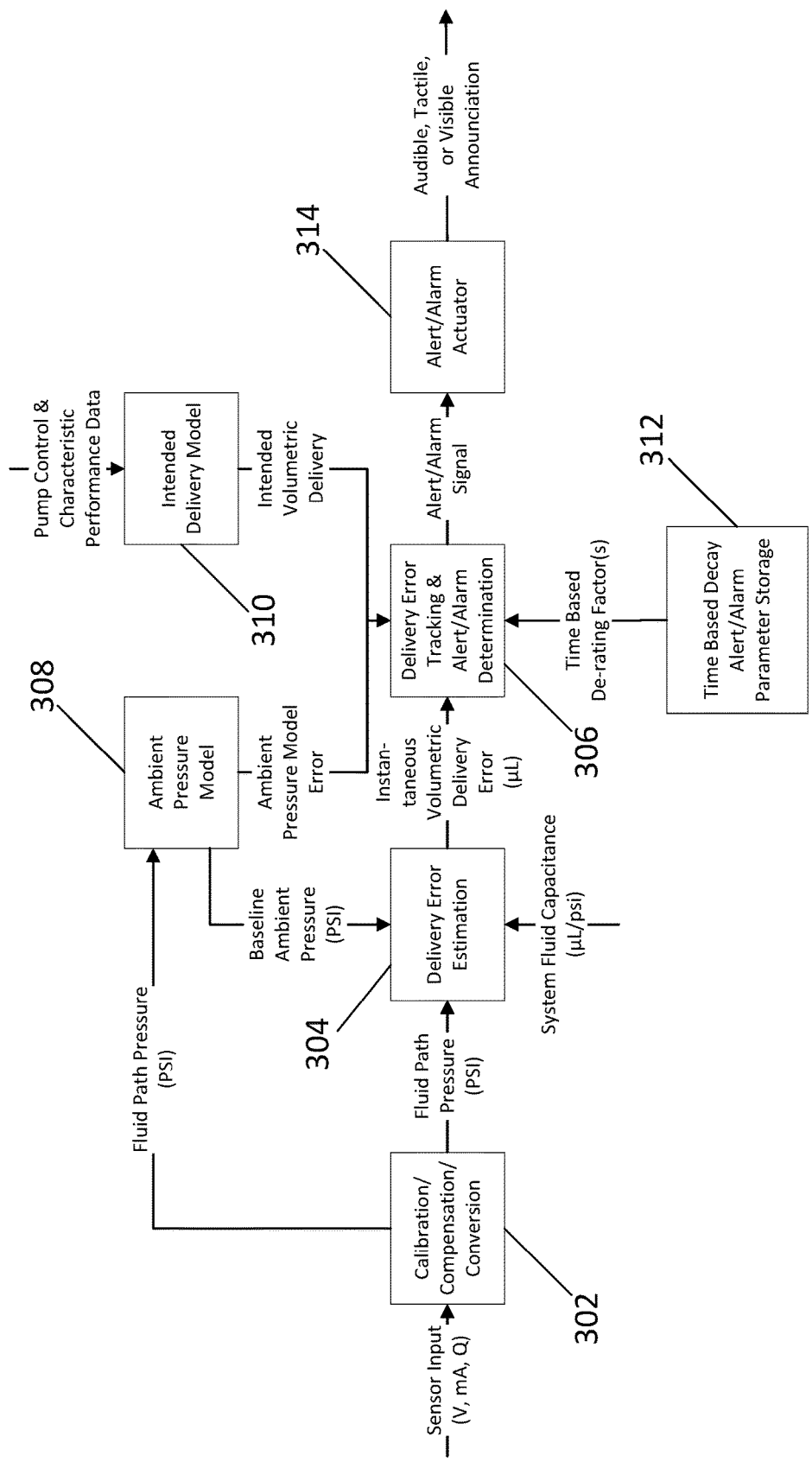
FIG. 3 illustrates a block diagram of operations performed by the pump system of FIG. 2.

FIG. 3 illustrates an operational block diagram 300 that shows operations for providing monitoring of any over-delivery or under-delivery condition during any intended or unintended drug delivery based on the pressure sensing described herein.

The operational block diagram 300 illustrates components that can be implemented by or can be included within the monitoring component 204 when implemented in conjunction with the pressure sensor 202. The operational block diagram 300 illustrates the inputs and outputs of each component and the function or capabilities of each components. The operations and components shown can be implemented in hardware, software, or any combination thereof.

The operational block diagram 300 can include the following components: a calibration-compensation-conversion component 302, a delivery error estimation component 304, a delivery error tracking and alarm determination 306, an ambient pressure model component 308, an intended delivery model 3108, a time-based decay alert-alarm parameter storage component 312, and an alert-alarm actuator component 314. The operations and functionalities of these components are described below.

The calibration-compensation-conversion component 302 can be coupled to a pressure sensor (e.g., the pressure sensor 202) and can receive one or more signals from the pressure sensor as described above. The calibration-compensation-conversion component 302 can also receive one or more signals relating to calibration, conversion, or compensation parameters. The calibration-compensation-conversion component 302 can operate to determine and output fluid path pressure (e.g., psi) based on the signals from the pressure sensor. Accordingly, the calibration-compensation-conversion component 302 can output a fluid path pressure signal. The calibration, conversion, or compensation parameters can also operate to provide sensor calibration and/or compensation functions such as, for example, linearization of output, input/output offset correction, and/or temperature compensation.

The delivery error estimation component 304 can receive the fluid path pressure output signal from the calibration-compensation-conversion component 302. The delivery error estimation component 304 can also receive fluid capacitance values (e.g., system calibration values) and baseline pressure values as shown in FIG. 3. The delivery error estimation component 304 can operate to determine instantaneous volumetric delivery error (e.g., an amount of under-delivery or over-delivery) and can output a signal indicating the same. To determine the instantaneous volumetric delivery error, the delivery error estimation component 304 can transform the provided pressure level relative to the pressure baseline into a delivery error by multiplying the pressure difference by the provided fluid capacitance value.

In various embodiments, to determine instantaneous volumetric delivery error, which can be represented as Verror(t), where "t" represent time, the delivery error estimate estimation component 304 can utilize a fluid capacitance value or values, which can be represented as Cfluid(ξ,t). Fluid capacitance is typically expressed in units of volume/pressure (e.g., in μL/psi for small pumping devices). "ξ" can represent an aggregated variability of the fluid capacitance which can vary both with time and with any number of system physical parameters (e.g., specific to each pumping device). The baseline ambient pressure, represented as P0(t), can be the baseline pressure at which the system is operating at any given time as provided by the ambient pressure model 308. The instantaneous fluid path pressure provided by the calibration-compensation-conversion component 302, represented as P(t), can be the instantaneous pressure measured at a given time. The instantaneous volumetric delivery error can therefore be expressed as: Verror(t)=[P(t)−P0(t)]*Cfluid (ξ,t).

The delivery error tracking and alarm determination component 306 can receive the instantaneous volumetric delivery error signal outputted by the delivery error estimation component 304. The delivery error tracking and alarm determination component 306 can also receive time-based de-rating factors, an ambient pressure model error, and an indication of intended volumetric delivery as shown in FIG. 3. Based on these input signals, the delivery error tracking and alarm determination component 306 can generate an alert or alarm signal as necessary, as described above. The delivery error tracking and alarm determination component 306 can compare the intended volumetric delivery against the sum of ambient pressure model error and instantaneous volumetric delivery error as modified by time-based de-rating factors. Threshold comparisons can also be made to determine if an alarm signal should be generated. If an alarm condition is determined, a signal indicating the same can be generated and outputted.

The ambient pressure model 308 can receive the fluid path pressure signal from the calibration-compensation-conversion component 302. The ambient pressure model 308 can output an ambient pressure model error. The ambient pressure model 308 can track background ambient pressure changes to limit false alarms due to ambient pressure or back pressure changes. The ambient pressure model 308 can also track background ambient pressure changes to determine over-delivery and/or under-delivery due to significant pressure excursions.

The intended delivery model component 310 can receive pump control data (e.g., a count of the number of pulses delivered) and can receive pump characteristic performance data (e.g., a measure of volume per pulse delivery). The intended delivery model component 310 generate an indication of expected volumetric delivery as shown in FIG. 3. The intended delivery model component 310 can track the expected delivery as commanded by the pump system for comparison in the delivery error tracking and alert-alarm determination component 306.

The time-based decay alert-alarm parameter storage 312 can receive and/or store system alert-alarm decay parameters. The time-based decay alert-alarm parameter storage 312 can output specific mathematical functions to de-rate the impact of instantaneous volumetric error over time. The time-based decay alert-alarm parameter storage 312 can ensure transient unintended delivery events do not accumulate in the system and lead to unnecessary alarms.

The alert-alarm actuator 314 can receive any alert-alarm signal from the delivery error tracking and alarm determination component 306. Based upon receipt of any alert-alarm signal, the alert-alarm actuator 314 can activate an alarm mechanism or component as described above including, for example, a visual, tactile, and/or audible alarm to notify the user of an urgent condition.

Figure 4:
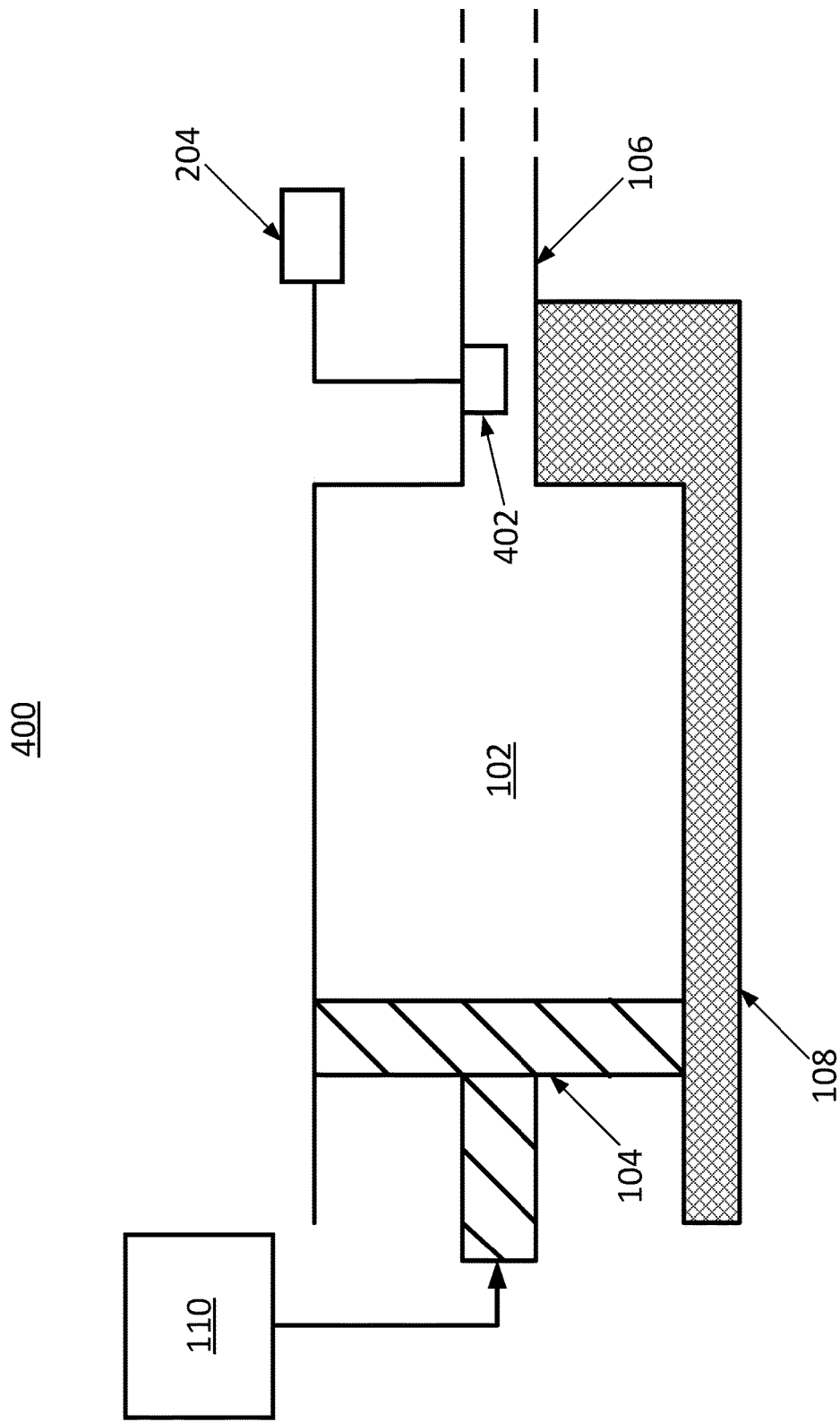
FIG. 4 illustrates a third exemplary pump system incorporating a flow sensor.

FIG. 4 illustrates a pump system 400 (or infusion pump system 400) for monitoring of any over-delivery or under-delivery condition during any intended or unintended drug delivery. As shown in FIG. 4, the pump system 400 can include the reservoir 102, the plunger 104, the fluid path component 106, a flow sensor 402, and the monitoring component 204. The pump system 400 can, among other features, detect unintended flow through flow sensing as described herein.

In contrast to the operation of the pump system 200 which can detect pressure and subsequently determine flow based on fluid capacitance of the fluid path of the pump system 200, the pump system 400 uses a flow sensor 402. The flow sensor 402 can be positioned directly in the flow path of the pump system 400 (e.g., in the fluid path component 106 as shown in FIG. 4). In various embodiments, the flow sensor 402 can sense flow (e.g., flow of the infusate) out of and into the fluid path of the pump system 400.

In general, the flow sensor 402 can be positioned anywhere along the fluid path of the pump system 400 including in a cannula coupled to the end of the fluid path component 106 leading to the patient. In various embodiments, the flow sensor 402 can be located just outside the reservoir 102 and before the hard cannula providing access to the patient. In various embodiments, the flow sensor 402 can be integrated into the hard cannula.

A variety of different types of flow sensors can be used for the flow sensor 402 such as, for example, a micro-electro-mechanical system (MEMS) thermal mass flow sensor, a paddle wheel, or other type flow sensor appropriately sized for the expected flow from the intended pumping action of the pump system 400 and/or the effect of ambient pressure changes on air trapped within the fluid path of the pump system 400.

The flow channel for the flow sensor 402 can be made from a variety of materials including, for example, glass, metal, or any other material that can provide adequate thermal conductance to detect changes in the thermal gradient in the flowing media (e.g., the infusate). The flow sensor 402 can be calibrated for the specific viscosity, thermal conductance, and flow channel convective coefficient, and external thermal changes (e.g., to provide temperature compensation).

The pump system 400 can provide similar functionality as the pump system 200 with the change of a flow sensor 402 being used instead of a pressure sensor as provided for in the pump system 200. To that end, the flow sensor 402 can be coupled to the monitoring component 204 with the monitoring component 204 configured to operate in conjunction with a flow sensor. The flow sensor 402 can take regular readings of flow through the fluid path of the pump system 400 and can output a signal to the monitoring component 204. The type of signal, format, and/or protocol of the signal of the output signal can be similar to the output signal provided by the pressure sensor 202 but with providing an indication of flow rather than pressure.

The monitoring component 204 can convert the signal from the flow sensor 402 to a measure of flow rate (e.g., in units of volume/time). In various embodiments, a flow rate in units of μL/minute can be used. In general, any representation of flow magnitude can be used.

To determine total flow over a given period of time, the monitoring component 204 can integrate the flow data to compute the total net volume dispensed over a given amount of time. This value of net total delivery can then be used to monitor over-delivery and/or under-delivery conditions during operation of the pump system 400 in a manner similar to that described above in relation to the pump system 200.

Accordingly, based on data or information provided by the flow sensor 402, the monitoring component 204 can monitor an amount of infusate delivered over time to determine if the amount is a proper or correct amount based on a predetermined level of intended infusate delivery. The monitoring component 204 can further determine if changes in physical conditions or the environment in which the pump system 400 operates can lead to under-delivery or over-delivery of the infusate during periods of intended delivery or intended non-delivery. The flow direction and the amount of fluid as determined by the monitoring component 204 can be compared to one or more operational thresholds, to determine if an alert should be issued to the patient. This allows the patient to more safely use the pump system 400 and to take corrective action if necessary.

Overall, the pump system 400 can monitor the same operation conditions and errors listed above in relation to the pump system 200 and can operate to provide the alarms indicated above as necessary based on monitoring flow direction and amount of flow during delivery periods and non-delivery periods (e.g., by monitoring net flow over set intervals of time of delivery or non-delivery). Accordingly, the discussion above of these features in relation to the pump system 200 are applicable to the pump system 400.

Further, the pump system 400 can adjust sampling of flow rates during (e.g., monitoring of flow rates) during periods of non-delivery—that is, during times when the pump system 400 is not being directed to specifically provide the infusate to the patient. Sampling of flow can be made continuously or semi-continuously to conserve power. In various embodiments, the pump system 400 can include an ambient pressure sensor to alter the flow sampling frequency in response to the potential for expansion or contraction of air bubbles in the fluid path. In various embodiments, the pump system 400—similar to the pump system 200—can include a temperature sensor to alter the flow sampling frequency in response to the potential for expansion or contraction of air bubbles in the fluid path, as described above in relation to the pump system 200.

Figure 5:
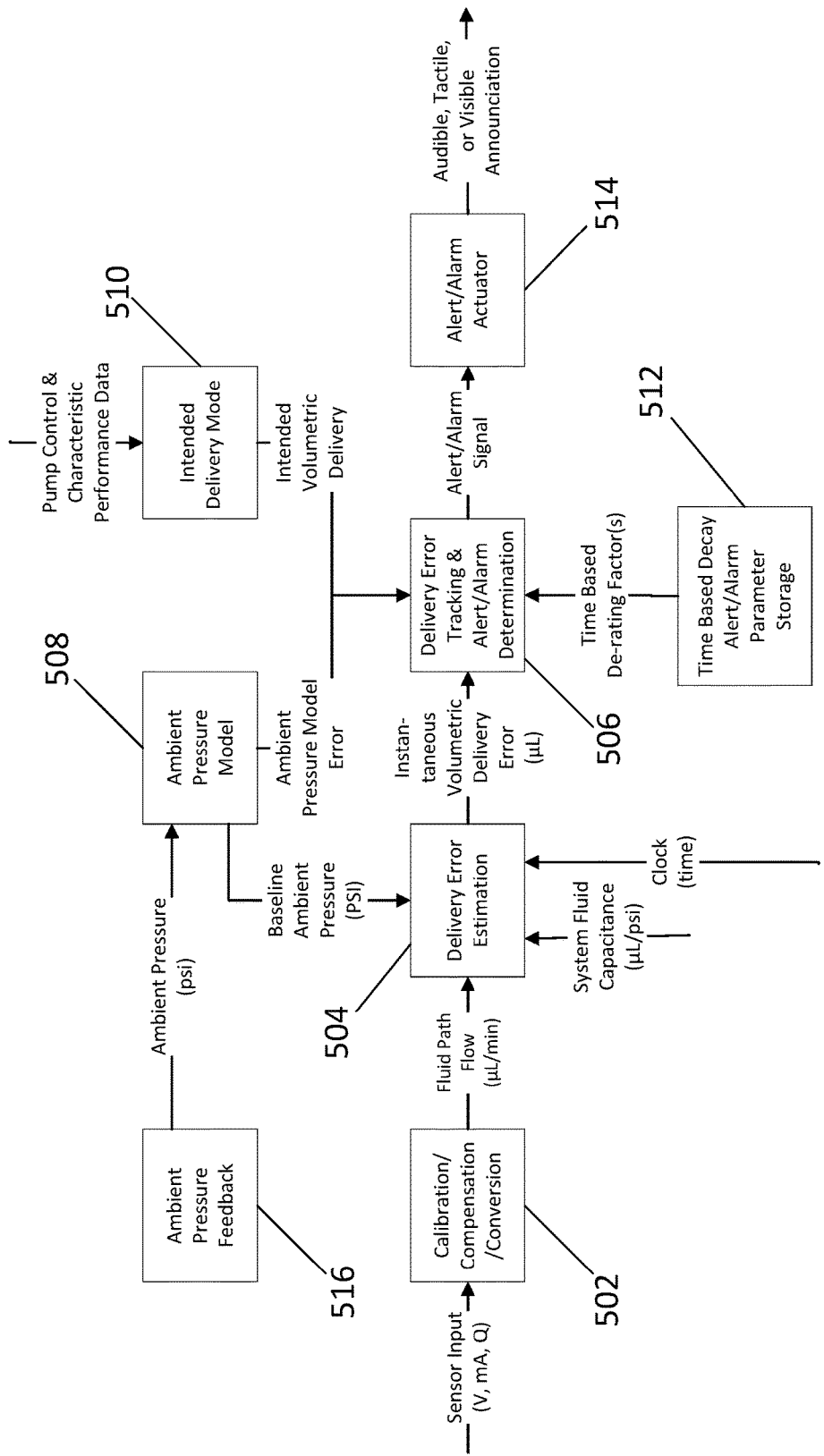
FIG. 5 illustrates a block diagram of operations performed by the pump system of FIG. 4.

FIG. 5 illustrates an operational block diagram 500 that shows operations for monitoring of any over-delivery or under-delivery condition during any intended or unintended drug delivery based on the flow sensing described herein. The operational block diagram 500 illustrates components that can be implemented by or can be included within the monitoring component 204 when implemented in conjunction with the flow sensor 402. The operational block diagram 500 illustrates the inputs and outputs of each component and the function or capabilities of each components. The operations and components shown can be implemented in hardware, software, or any combination thereof.

The operational block diagram 500 can include the following components: a calibration-compensation-conversion component 502, a delivery error estimation component 504, a delivery error tracking and alarm determination 506, an ambient pressure model component 508, an intended delivery model 510, a time-based decay alert-alarm parameter storage component 512, and an alert-alarm actuator component 514, and an ambient pressure feedback component 516. The operations and functionalities of these components are described below.

The calibration-compensation-conversion component 502 can be coupled to a flow sensor (e.g., the flow sensor 402) and can receive one or more signals from the flow sensor as described above. The calibration-compensation-conversion component 502 can also receive one or more signals relating to calibration, conversion, or compensation parameters. The calibration-compensation-conversion component 502 can operate to determine and output fluid path flow (e.g., μL/min) based on the signals from the flow sensor. Accordingly, the calibration-compensation-conversion component 502 can output a fluid path flow signal indicating instantaneous flow rate. The calibration, conversion, or compensation parameters can also operate to provide sensor calibration and/or compensation functions such as, for example, linearization of output, input/output offset correction, and/or temperature compensation.

The delivery error estimation component 504 can receive the fluid path instantaneous flow rate output signal from the calibration-compensation-conversion component 502. The delivery error estimation component 504 can also receive fluid capacitance values (e.g., system calibration values), ambient pressure baseline values, and a clock signal (e.g., from an external clock) as shown in FIG. 5. The delivery error estimation component 504 can operate to determine instantaneous volumetric delivery error (e.g., an amount of over-delivery or under-delivery) and can output a signal indicating the same. To determine the instantaneous volumetric delivery error, the delivery error estimation component 504 can integrate indicators of fluid path flow to determine instantaneous volumetric flow error. The delivery error estimation component 504 can also compensate for ambient pressure changes which could cause unintended flow to occur.

The delivery error tracking and alarm determination component 506 can receive the instantaneous volumetric delivery error signal outputted by the delivery error estimation component 504. The delivery error tracking and alarm determination component 506 can also receive time-based de-rating factors, an ambient pressure model error, and an indication of intended volumetric delivery as shown in FIG. 5. Based on these input signals, the delivery error tracking and alarm determination component 506 can generate an alert or alarm signal as necessary as described above. The delivery error tracking and alarm determination component 506 can compare the intended volumetric delivery against the sum of ambient pressure model error and instantaneous volumetric delivery error as modified by time based de-rating factors. Threshold comparisons can also be made to determine if an alarm signal should be generated. If an alarm condition is determined, a signal indicating the same can be generated and outputted.

The ambient pressure model 508 can receive an ambient pressure signal from the ambient pressure feedback component 516. The ambient pressure model 508 can output an ambient pressure model error. The ambient pressure model 508 can track background ambient pressure changes to limit false alarms due to ambient pressure or back pressure changes. The ambient pressure model 508 can also track background ambient pressure changes to determine over-delivery and/or under-delivery due to significant pressure excursions.

The intended delivery model component 510 can receive pump control data (e.g., a count of the number of pulses delivered) and can receive pump characteristic performance data (e.g., a measure of volume per pulse delivery). The intended delivery model component 510 can generate an indication of expected volumetric delivery as shown in FIG. 5. The intended delivery model component 510 can track the expected delivery as commanded by the pump system for comparison in the delivery error tracking and alert-alarm determination component 506.

The time-based decay alert-alarm parameter storage 512 can receive and/or store system alert-alarm decay parameters. The time-based decay alert-alarm parameter storage 512 can output specific mathematical functions to de-rate the impact of instantaneous volumetric error over time. The time-based decay alert-alarm parameter storage 512 can ensure transient unintended delivery events do not accumulate in the system and lead to unnecessary alarms.

The alert-alarm actuator 514 can receive any alert-alarm signal from the Delivery error tracking and alarm determination component 506. Based upon receipt of any alert-alarm signal, the Alert-alarm actuator 514 can activate an alarm mechanism as described above including, for example, a visual and/or audible alarm to notify the user of an urgent condition.

The ambient pressure feedback component 516 can provide ambient pressure feedback (e.g., in psi) via an absolute pressure sensor (e.g., not sensing the fluid path). This ambient pressure feedback component 516 can be optional to help account for events in between flow sampling.

Figure 6:
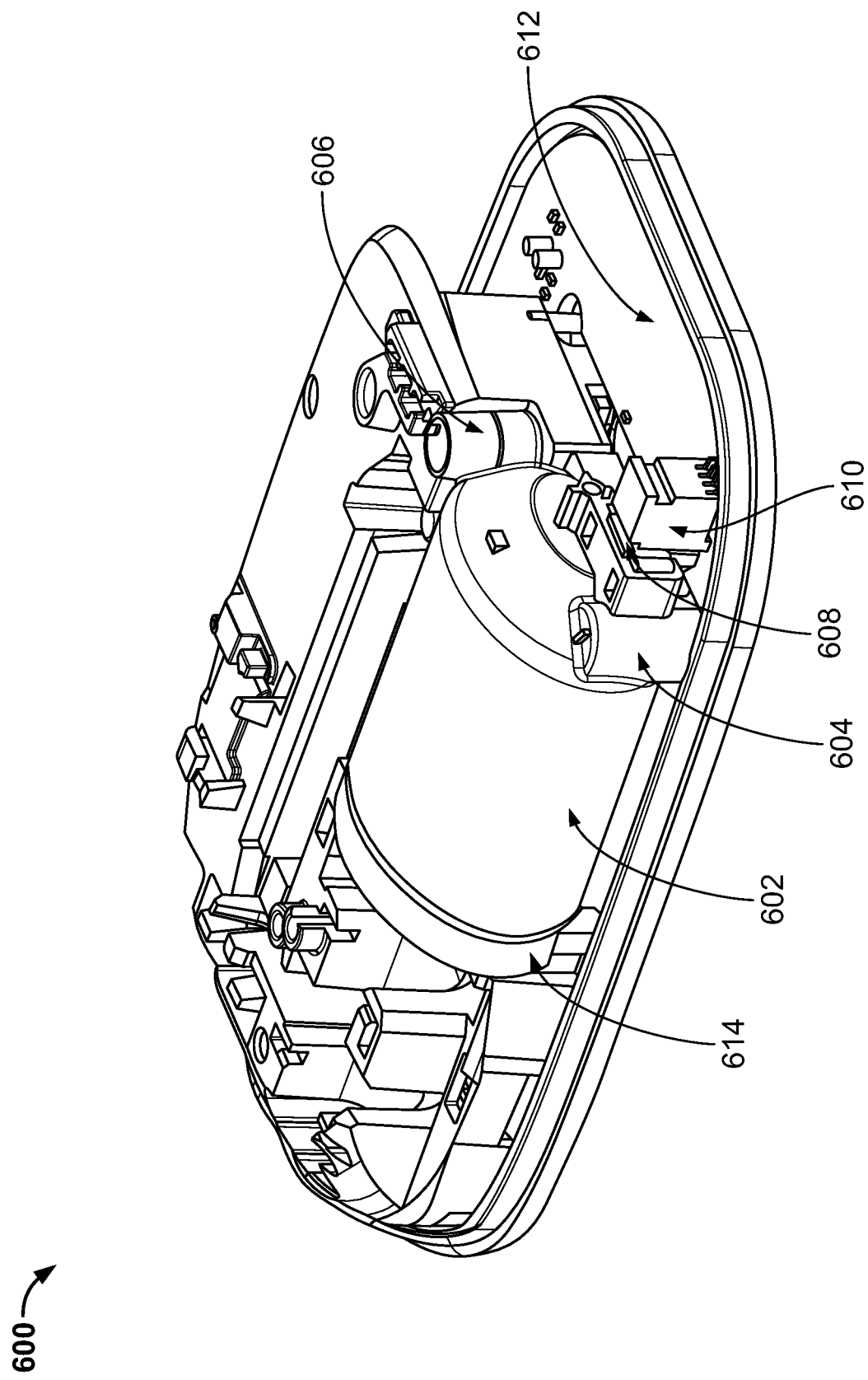
FIG. 6 illustrates an exemplary drug delivery device.

FIG. 6 illustrates an exemplary drug delivery device 600. The drug delivery device 600 can represent any of the drug delivery devices described herein. The drug delivery device 600 can be a wearable drug delivery device. The drug delivery device 600 can be designed to deliver any type of drug, medicine, therapeutic agent, or infusate to a user such as, for example, insulin. The drug delivery device 600 can be a single-use device (e.g., filled once and used once and then discarded) or can be a multiple-use device (e.g., filled one or more times and used after one or more fillings).

In various embodiments, the drug delivery device 100 can be provided to a user without any included drug or medicine. Under such a scenario, a user may, for example, fill a reservoir of the drug delivery device 600 with a medicine or drug (e.g., by transferring a fluid from a syringe to a reservoir of the drug delivery device 600).

The drug delivery device 600 can be an infusion device, including a drug delivery pump device as described herein. The drug delivery device 600 may provide a stored drug to a user over a relatively long period of time (e.g., over several days in small dosage amounts) or over a relatively short period of time (e.g., over a few hours to a day). In various embodiments, the drug delivery device 600 can be an OmniPod® (Insulet Corporation, Billerica, Mass.) insulin delivery device. The drug delivery device 600 can be a drug delivery device such as those described in U.S. Pat. Nos. 7,303,549, 7,137,964, or 6,740,059, each of which is incorporated herein by reference in its entirety.

In various embodiments, the drug delivery device can include the pump systems described herein including the pump system 200 or the pump system 400 as well as the corresponding implementations of the monitoring component 204 described in relation to FIGS. 3 and 5, respectively. Overall, the drug delivery device 100 can include the monitoring of over-delivery and under-delivery of an infusate to a patient during intended delivery periods and intended non-delivery periods according to the techniques described herein.

Various internal constituent components of the drug delivery device 600 are shown in FIG. 6. A top or cover of the drug delivery device 600 is not shown so as to provide a view of the various internal components and features of the drug delivery device 600. As shown in FIG. 6, the drug delivery device 600 can include a reservoir or pump reservoir 602, a reservoir inlet 604, a reservoir outlet 606, a sensor 608, a sensor assembly 610, a printed circuit board assembly (PCBA) 612, and structural support component 614.

The pump reservoir 602 can hold or store the drug or medicine that can be delivered to a user (e.g., insulin). The pump reservoir 602 can be accessed or filled through the reservoir inlet 604. The reservoir inlet 604 can provide a path for transferring a fluid from outside of the drug delivery device 600 to inside the drug delivery device 600 for storage and subsequent delivery. The drug stored in the pump reservoir 602 can exit the pump reservoir 602 through the reservoir outlet 606 for delivery to the user. The drug delivery device 600 can include a pump for transferring the drug from the reservoir 602 to a user. In various embodiments, a plunger acting in conjunction with the reservoir 602 can operate as a pump to enable the stored fluid to be expelled for delivery to a patient through a fluid path (e.g., as described in relation to the pumps systems 200 and 400). When extracted by operation of the pump, the drug may follow a path from the reservoir 602 to an outlet of the drug delivery device 602 and then on to a patient.

The sensor 608 can be a pressure sensor (e.g., the pressure sensor 202) and can operate and provide the functionality described above. The sensor 608 can be incorporated into the fluid path of the drug delivery device 600 (e.g., incorporated into the reservoir 602). The sensor 608 can be coupled to a sensor assembly or sensor interface 610. The sensor assembly 610 can provide connectivity between the sensor 608 and the PCBA 612. The PCBA 612 can house or contain additional functional components for operating the drug delivery device 600 including, for example, a controller for operating the drug pump to deliver stored fluid from the reservoir 602 to the user. The PCBA 612 can further house or contain components related to user interaction or control components as well as user feedback components including, such as, any of the alarm mechanisms or components described herein. Signals can be transferred bidirectionally between the sensor 608 and the PCBA 612 (and any other components coupled to the PCBA 612) by way of the interface 610. The monitoring component 204 can be integrated across any number of components included in the drug delivery device 600 and can, in various embodiments, include a processor and associated memory, dedicated hardware, or any device capable of executing instructions (e.g., computer executable code, firmware, etc.).

The structural support component 614 can correspond to the structural support component 108 represented in FIGS. 1, 2, and 4. The structural support component 614 can provide mechanical structural support for the reservoir 602 as well as the plunger and fluid path of the drug delivery device 600 and so can include any component of the drug delivery device 600 that supports these components.

Figure 11:
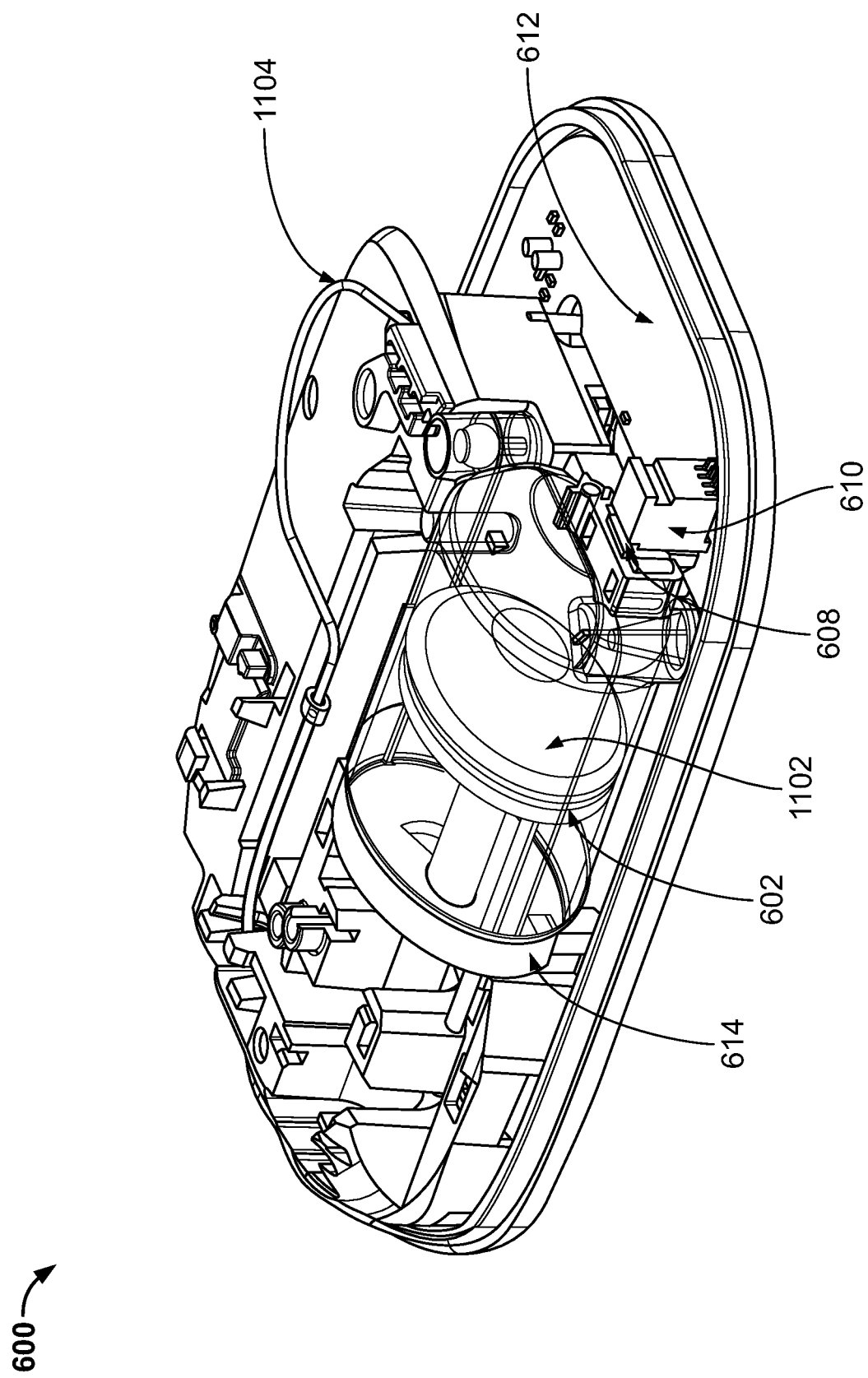
FIG. 11 illustrates a second view of the exemplary drug delivery device of FIG. 6.

FIG. 11 illustrates the drug delivery device 600 depicted in FIG. 6 with a transparent version of the reservoir 602 to reveal additional detail of the drug delivery device 600. As shown in FIG. 11, the drug delivery device 600 includes a plunger 1102 that can be positioned within the reservoir 602. An end portion or stem of the plunger 1102 can extend outside of the reservoir 602. The plunger 1102 can expel the liquid drug from the reservoir 602 by advancing into the reservoir 602. The plunger 1102 can be advanced by a plunger or pump drive mechanism that can be coupled to the plunger 1102 as described above (not illustrated in FIG. 11 for simplicity).

FIG. 11 further illustrates a fluid path component 1104. The fluid path component 1104 can couple the reservoir 602 to a user of the drug delivery device 600. The liquid drug expelled from the reservoir 602 can be provided to the patient by way of the fluid path component 1104. The fluid path component 1104 can correspond to the representation of the fluid path component 106 depicted in FIGS. 1, 2, and 4.

FIGS. 7-10 illustrates various techniques for incorporating a pressure sensor (e.g., the pressure sensor 202) into the fluid path of a pump system—in particular, a pump system included within the drug delivery device 600.

Figure 7:
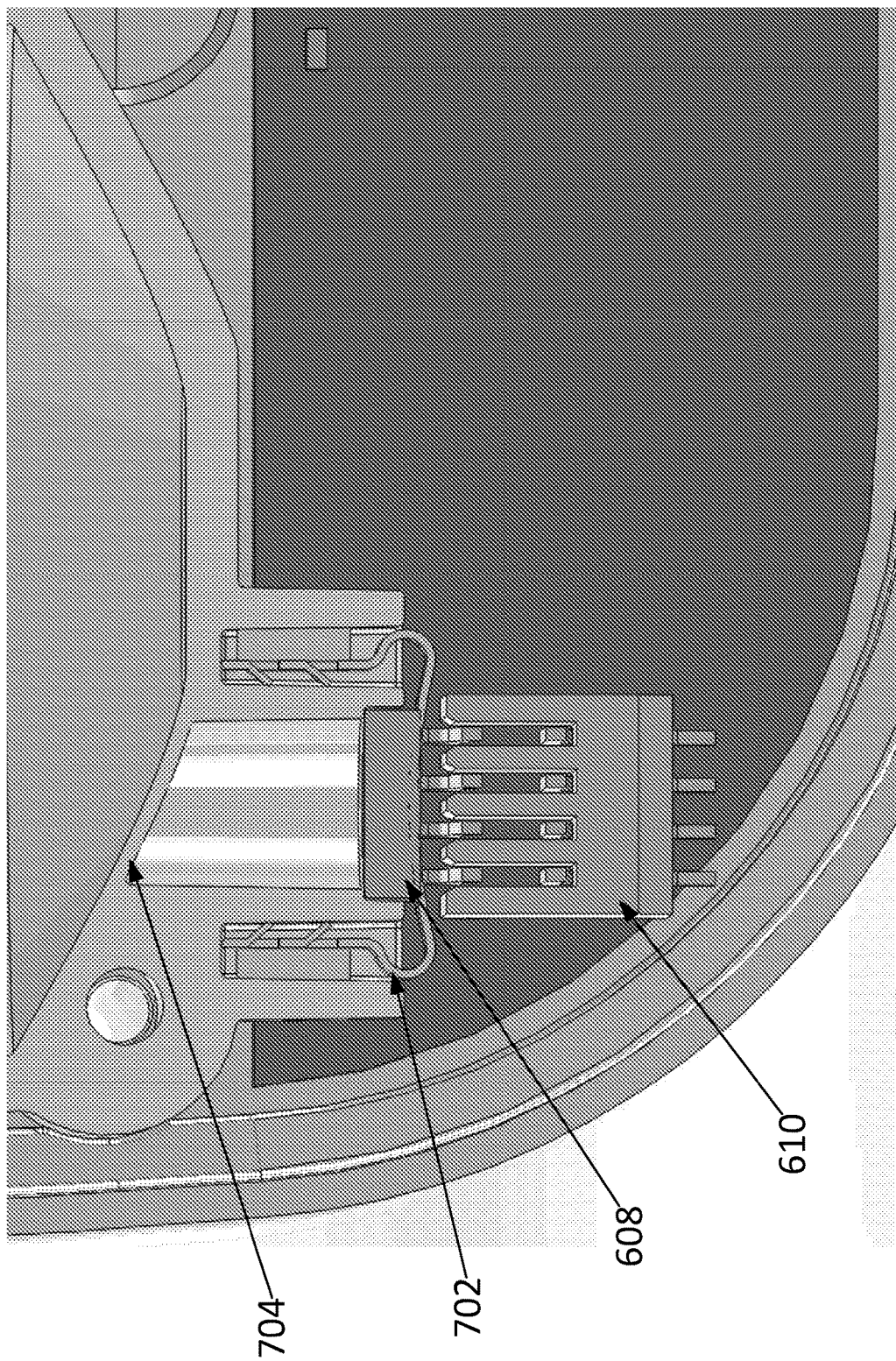
FIG. 7 illustrates a first exemplary incorporation of a pressure sensor into the drug delivery device of FIG. 6.

FIG. 7 illustrates a sensor retention clip 702 coupled to the sensor 608 and a pressure transfer membrane 704. The pressure transfer membrane 704 can isolate the sensor 608 from the fluid path—for example, a liquid drug stored in the reservoir 602. The pressure transfer membrane 704 can react to a displacement force caused by, for example, a pumping action to expel a liquid drug from the reservoir 602. The sensor retention clip 702 can help maintain a positioning of the sensor 608 as it responds to (e.g., and monitors and/or measures) changes in pressure that may be caused by any displacement force. A force transfer potting (not shown in FIG. 7 for simplicity) can be used to transfer changes in pressure for measurement by the sensor 608 and can be positioned between the sensor 608 and the membrane 704.

Figure 8:
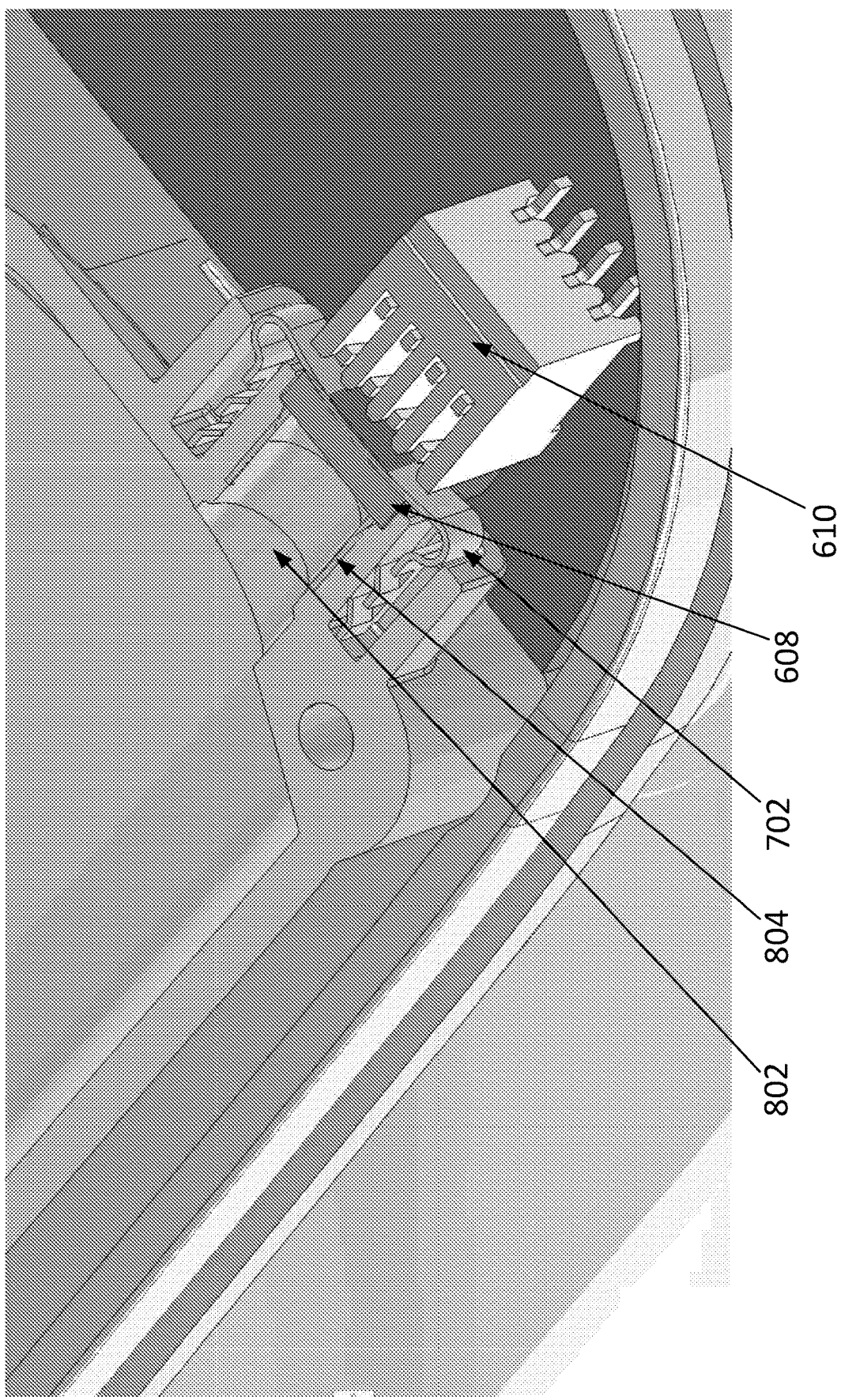
FIG. 8 illustrates a second exemplary incorporation of a pressure sensor into the drug delivery device of FIG. 6.

FIG. 8 illustrates the sensor 608 positioned within a pressure sensor installation port 802. The sensor 608, as described above, can have a round shape and can be fitted into the installation port 802 to form a tight fit with the reservoir 602. The sensor 608 can include a portion 804 that extends into the installation port 802. The sensor 608 and portion 804 can be isolated from the fluid path of the drug delivery device 600 by the walls of the reservoir 602 and the sensor 608 and extended portion 804. The sensor 608 and the extended portion 804 can be pressed into an undersized bore forming a portion of the installation port 802 to ensure an air-tight and liquid-tight seal (e.g., a hermetic seal). The engagement of the sensor 608 with the fluid path as shown in FIG. 8 can be considered to be a long engagement press fit. The arrangement shown in FIG. 8 can further include force transfer potting (not shown in FIG. 8 for simplicity) as will be understood by a person of ordinary skill in the art.

Figure 9:
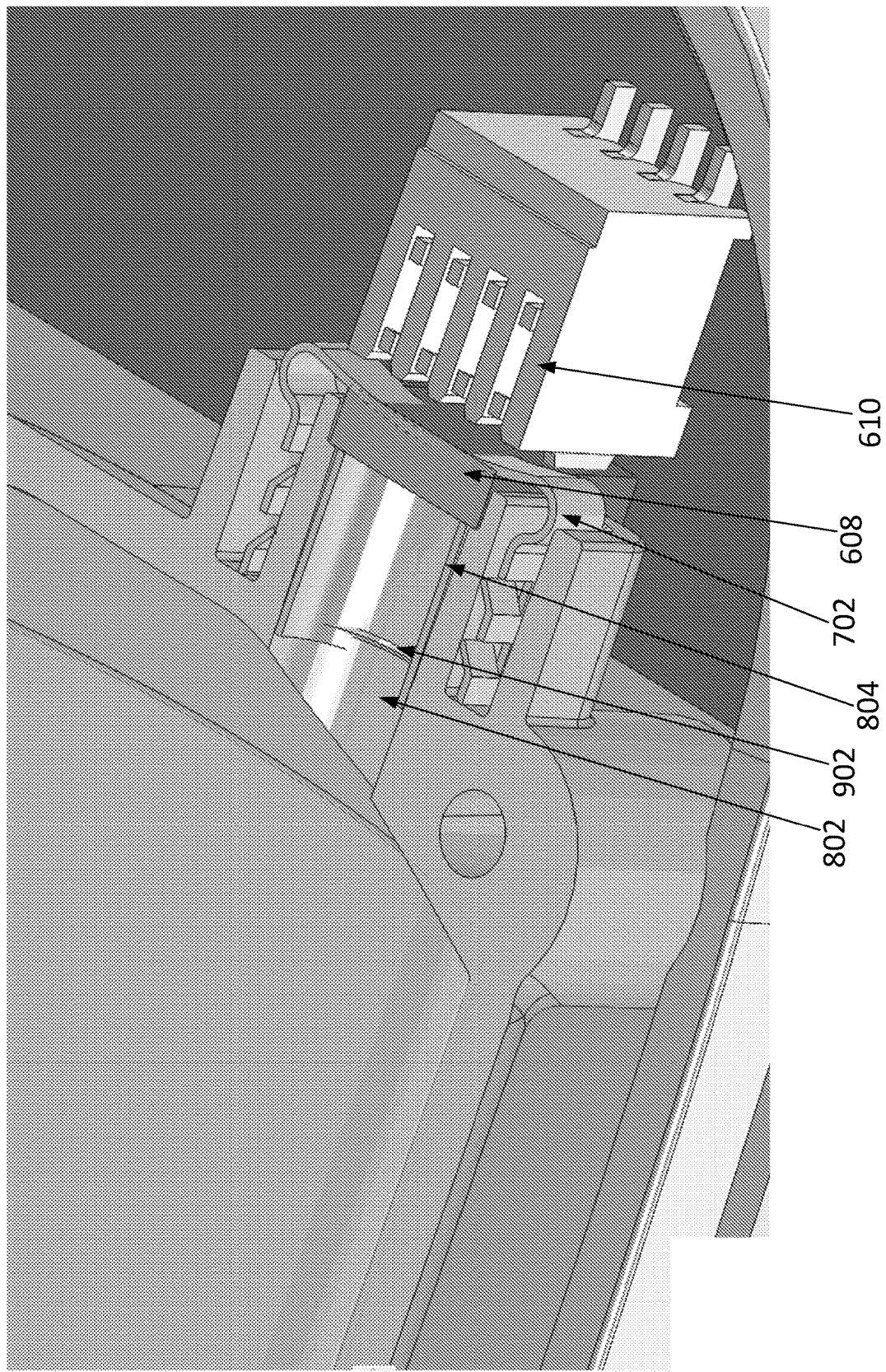
FIG. 9 illustrates a third exemplary incorporation of a pressure sensor into the drug delivery device of FIG. 6.

FIG. 9 illustrates the sensor 608 positioned within the pressure sensor installation port 802 and an integral radial point seal 902 positioned with the installation port 802. The radial seal 902 can be positioned anywhere along the extended portion 804 and can be molded into the walls of the reservoir 602/installation port 802. The radial seal 902 can further help isolate the sensor 608 from the fluid path of the drug delivery device 600. The arrangement shown in FIG. 9 can further include force transfer potting (not shown in FIG. 9 for simplicity) as will be understood by a person of ordinary skill in the art.

Figure 10:
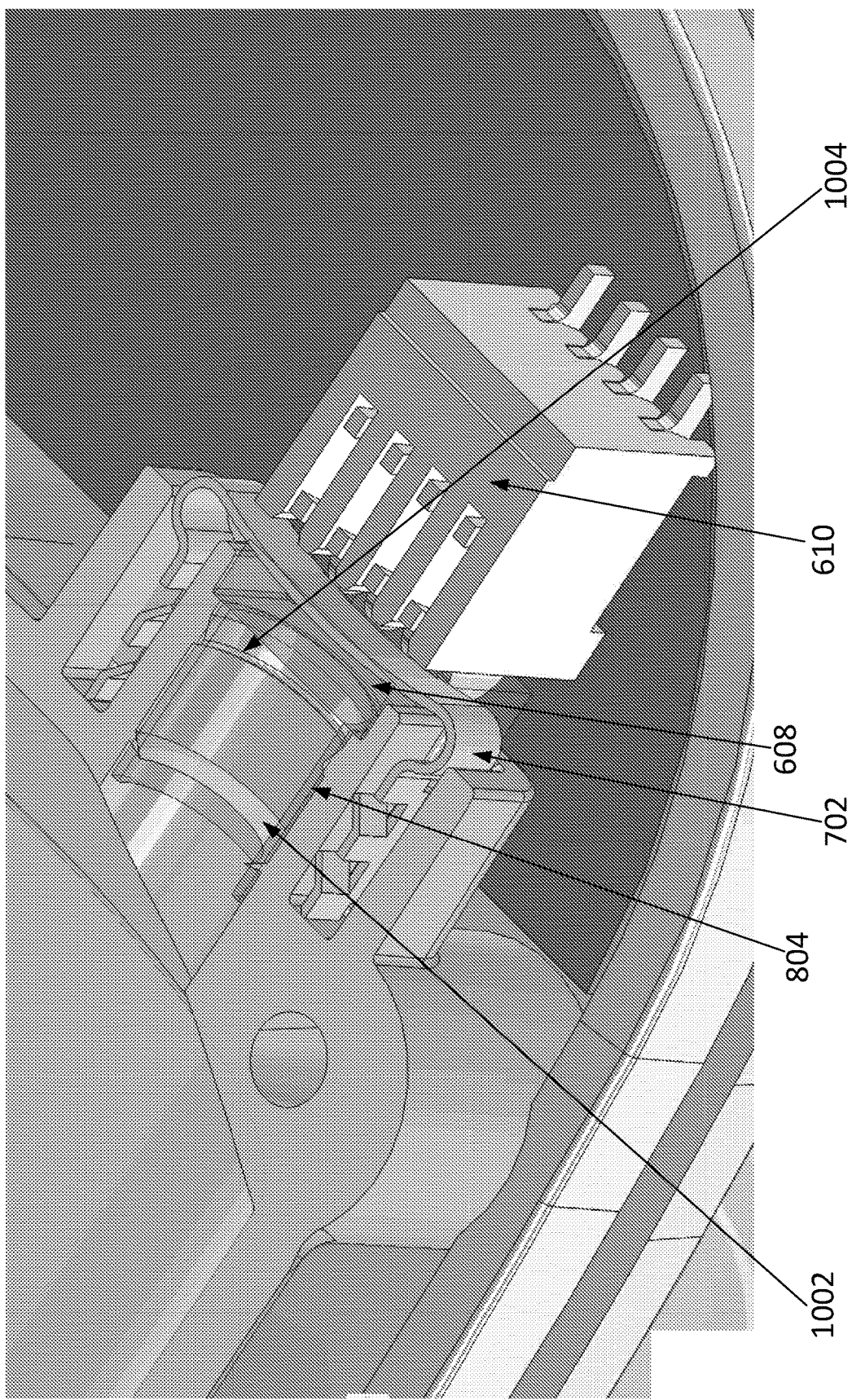
FIG. 10 illustrates a fourth exemplary incorporation of a pressure sensor into the drug delivery device of FIG. 6.

FIG. 10 illustrates the sensor 608 positioned within the pressure sensor installation port 802 and a radial lip seal 1002 and a radial point seal 1004. The radial lip seal 1002 and the radial point seal 1004 can be molded into the walls of the reservoir 602/installation port 802. The sensor 608 and extended portion 804 thereof can be pressed into the installation port 802 and can engage the radial lip seal 1002 and the radial point seal 1004. The radial lip seal 1002 radially extends into an open area of the installation port 802. The radial lip seal 1002 can form a pointed end feature that can bend out of the way when the sensor 608 and extended portion 804 are pressed into the installation port 802. The radial lip seal 1002 provides a further isolating sealing feature. Pressure can cause the seal between the sensor 608, the extended portion 804, and/or the walls of the reservoir 602 to engage the radial lip seal 1002 in a tighter manner, thereby resulting in a better or tighter seal as pressure increases (e.g., as more of the liquid drug is expelled from the reservoir 602). The arrangement shown in FIG. 10 can further include force transfer potting (not shown in FIG. 10 for simplicity) as will be understood by a person of ordinary skill in the art.

In various embodiments, during an operation to provide a drug to a user, when a pump pulse occurs, a sharp rise in pressure can be sensed, followed by a slow decay as the pulse exits a narrow pump cannula of a drug delivery device. By monitoring the pressure spike and the corresponding decay, any of the pump systems (e.g., pump systems 200 or 400) or drug delivery devices described herein can determine if fluid is flowing, or if there is in an occlusion.

Pressure spikes that may occur when a pulse is not being delivered can be due to external effects (e.g., flying, swimming, physiological changes). By comparing pressure changes to the characteristic fluid capacitance, techniques described herein can determine if unexpected under-delivery or over-delivery of the drug has occurred in real time. Further, by comparing delivery conditions to a baseline and non-delivery conditions to the baseline, under-delivery and over-delivery conditions may be detected, as described herein.

The pump systems (e.g., pump systems 200 or 400) or drug delivery devices described herein, including techniques described herein performed by these devices, can provide numerous benefits over conventional drug delivery devices. In particular, the techniques described herein can provide virtual real-time occlusion detection. Further, the techniques can distinguish an occlusion (e.g., a no flow or low flow condition) from an increase in back pressure (e.g., increased resistance with continual flow). Additionally, the techniques described herein can track and log data (e.g., pressure change information) related to excursions from stated altitude or depth specifications.

The following examples pertain to additional further embodiments:

Example 1 is a method comprising determining a first pressure at a start of a delivery operation for a liquid drug, determining a second pressure at an end of the delivery operation for the liquid drug, determining a fluid capacitance value of a fluid path used for the delivery operation of the liquid drug, and determining an intended liquid drug delivery amount, and determining a delivery error amount of the liquid drug based on the first and second pressures, the fluid capacitance value, and the intended liquid drug delivery amount.

Example 2 is an extension of Example 1 or any other example disclosed herein, further comprising determining the first and second pressures based on determining an absolute pressure.

Example 3 is an extension of Example 2 or any other example disclosed herein, further comprising comparing the delivery error amount to one or more thresholds.

Example 4 is an extension of Example 3 or any other example disclosed herein, further comprising determining an over-delivery condition when the delivery error amount is greater than a first threshold.

Example 5 is an extension of Example 4 or any other example disclosed herein, further comprising determining an under-delivery condition when the delivery error amount is less than a second threshold.

Example 6 is an extension of Example 5 or any other example disclosed herein, further comprising providing a first alarm in response to the over-delivery condition and providing a second, different alarm in response to the under-delivery condition.

Example 7 is an extension of Example 6 or any other example disclosed herein, wherein the first and second alarms comprise at least one of an audible, a visual, and a tactile indication.

Example 8 is an extension of Example 7 or any other example disclosed herein, further comprising adjusting an indication of urgency of at least one of the first and second alarms based on a determined severity of the over-delivery condition and the under-delivery condition, respectively.

Example 9 is an extension of Example 6 or any other example disclosed herein, further comprising dynamically adjusting the first and second thresholds.

Example 10 is an extension of Example 9 or any other example disclosed herein, further comprising dynamically adjusting the first and second thresholds based on a de-rating factor based on a determined total amount of delivered liquid drug.

Example 11 is an extension of Example 9 or any other example disclosed herein, further comprising dynamically adjusting the first and second thresholds based on a de-rating factor based on a determined unmetabolized excess amount of over-delivered liquid drug.

Example 12 is an extension of Example 9 or any other example disclosed herein, further comprising determining a rate of change of atmospheric pressure.

Example 13 is an extension of Example 12 or any other example disclosed herein, further comprising dynamically adjusting the first and second thresholds based on the determined rate of change of the atmospheric pressure.

Example 14 is an extension of Example 9 or any other example disclosed herein, further comprising determining a temperature.

Example 15 is an extension of Example 14 or any other example disclosed herein, further comprising dynamically adjusting the first and second thresholds based on the determined temperature.

Example 16 is an extension of Example 1 or any other example disclosed herein, further comprising determining an unintended delivery error amount of the liquid drug during a time outside of the delivery operation of the liquid drug.

Example 17 is an extension of Example 16 or any other example disclosed herein, further comprising comparing the unintended delivery error amount to one or more unintended delivery thresholds.

Example 18 is an extension of Example 17 or any other example disclosed herein, further comprising providing an alarm responsive to comparing the unintended delivery error amount to the one or more unintended delivery thresholds.

Example 19 is an apparatus comprising a reservoir configured to hold a liquid drug, a fluid path component configured to couple the reservoir to a user, a plunger configured to expel the liquid drug from the reservoir for delivery to the user, an absolute pressure sensor configured to detect atmospheric pressure and relative pressure, and a monitoring component configured to determine a delivery error amount during an intended delivery operation and an unintended delivery operation based on the atmospheric pressure and the relative pressure.

Example 20 is an extension of Example 19 or any other example disclosed herein, wherein the plunger is directed to expel the liquid drug from the reservoir during an intended delivery operation and is directed to not expel the liquid drug from the reservoir during an unintended delivery operation.

Example 21 is an extension of Example 20 or any other example disclosed herein, wherein the monitoring component indicates an over-delivery condition when the delivery error amount is greater than a first threshold and wherein the monitoring component indicates an under-delivery condition when the delivery error amount is less than a second, different threshold.

Example 22 is an extension of Example 21 or any other example disclosed herein, wherein the monitoring component is configured to generate an alarm signal based on a determined severity of at least one of the over-delivery condition and the under-delivery condition.

Example 23 is an extension of Example 22 or any other example disclosed herein, wherein the alarm signal comprises at least one of a visual, an audible, and a tactile alert.

Example 24 is an extension of Example 21 or any other example disclosed herein, wherein the monitoring component is configured to dynamically adjust the first and second thresholds.

Example 25 is an extension of Example 24 or any other example disclosed herein, further comprising a temperature sensor, the monitoring component configured to dynamically adjust the first and second thresholds based on at least one of a determined temperature and a de-rating factor based on a determined total amount of delivered liquid drug.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. An apparatus, comprising:
a reservoir configured to hold a liquid drug;
a fluid path component configured to be coupled to the reservoir;
a plunger configured to expel the liquid drug from the reservoir for delivery via the fluid path component;
a pressure transfer membrane coupled to the reservoir and operable to detect a pressure change within the reservoir;
a pressure sensor coupled to the pressure transfer membrane, wherein the pressure sensor is configured to detect atmospheric pressure and relative pressure from the pressure transfer membrane and output signals based on the detected atmospheric pressure and relative pressure;
a sensor interface coupled to the pressure sensor and operable to receive the signals output by the pressure sensor based on the detected atmospheric pressure and relative pressure; and
a monitoring component coupled to the sensor interface including circuitry, wherein the circuitry is operable to:
receive a first signal indicative of a first pressure from the sensor interface;
receive a second signal indicative of a second pressure from the sensor interface;
determine a delivery error amount of the liquid drug based on the first pressure and the second pressure;
actuate an alarm actuator to activate an alarm when a first threshold or a second threshold is passed.

2. The apparatus of claim 1, wherein the pressure transfer membrane is operable to isolate the pressure sensor from the liquid drug.

3. The apparatus of claim 1, wherein the pressure transfer membrane is operable to react to a displacement force caused by a pumping action to expel a liquid drug from the reservoir.

4. The apparatus of claim 1, wherein the plunger is directed to expel the liquid drug from the reservoir during an intended delivery operation and is directed to not expel the liquid drug from the reservoir during an unintended delivery operation.

5. The apparatus of claim 1, wherein:
the first pressure is a pressure at a start of a delivery operation for the liquid drug,
the second pressure is a pressure at an end of the delivery operation for the liquid drug, and
the circuitry of the monitoring component is configured to:
determine a fluid capacitance value of a fluid path used for the delivery operation of the liquid drug based on the first pressure and the second pressure;
determine an intended liquid drug delivery amount; and
determine the delivery error amount of the liquid drug based on the first pressure, the second pressure, the fluid capacitance value, and the intended liquid drug delivery amount.

6. The apparatus of claim 5, wherein the alarm comprises at least one of a visual, an audible, and a tactile alert.

7. The apparatus of claim 1, wherein the monitoring component indicates:
an over-delivery condition when the delivery error amount is greater than the first threshold, and
an under-delivery condition when the delivery error amount is less than the second threshold.

8. The apparatus of claim 7, wherein the monitoring component is configured to generate the alert-alarm signal based on a determined severity of the over-delivery condition or the under-delivery condition.

9. The apparatus of claim 7, wherein the monitoring component is configured to dynamically adjust the first and second thresholds.

10. The apparatus of claim 7, further comprising:
a temperature sensor operable to provide a measure of temperature to the monitoring component, wherein the monitoring component is further configured to dynamically adjust the first and second thresholds based on a measured temperature or a de-rating factor based on a determined total amount of delivered liquid drug.

11. The apparatus of claim 5, wherein the first signal is received at a first point in time and the second signal is received at a second point in time later than when the first signal is received.

12. The apparatus of claim 5, wherein the fluid capacitance value changes in response to effective stiffness of a reservoir containing the liquid drug as the plunger is advanced further into the reservoir by a plunger drive mechanism coupled to the monitoring component.

13. An apparatus, comprising:
a reservoir configured to hold a liquid drug;
a fluid path component configured to form a fluid path from the reservoir;
a plunger configured to expel the liquid drug from the reservoir for delivery of the liquid drug via the fluid path formed by the fluid path component;
a pressure sensor installation port adjacent to the reservoir;
a pressure sensor operable to fit into the pressure sensor installation port, wherein:
the pressure sensor is configured to detect pressure from a pressure transfer membrane and output signals based on the detected pressure of the fluid path, and
the pressure sensor installation port is operable to isolate the pressure sensor from the fluid path;
a sensor interface coupled to the pressure sensor and operable to receive to the signals output by the pressure sensor based on the detected pressure; and
a monitoring component coupled to the sensor interface including circuitry, wherein the circuitry is operable to:
receive a first signal indicative of a first pressure from the sensor interface;
receive a second signal indicative of a second pressure from the sensor interface;
determine a delivery error amount of the liquid drug based on the first pressure and the second pressure; and
actuate an alarm actuator to activate an alarm when a first threshold or a second threshold is passed.

14. The apparatus of claim 13, wherein the pressure sensor further comprises:
an extended portion, wherein the extended portion is operable to couple to the pressure sensor installation port to create a hermetic seal.

15. The apparatus of claim 14, further comprising:
a radial point seal positioned within the installation port and operable to further isolate the pressure sensor from the fluid path of the reservoir, wherein the radial point seal is positionable along the extended portion.

16. The apparatus of claim 14, further comprising:
a radial lip seal positioned within the installation port and forming a pointed end feature that is operable to bend when the pressure sensor and the extended portion are inserted into the installation port.

17. The apparatus of claim 13, wherein the plunger is directed to expel the liquid drug from the reservoir during an intended delivery operation and is directed to not expel the liquid drug from the reservoir during an unintended delivery operation.

18. The apparatus of claim 13, wherein:
the first pressure is a pressure at a start of a delivery operation for the liquid drug,
the second pressure is a pressure at an end of the delivery operation for the liquid drug, and
the circuitry of the monitoring component is configured to:
determine a fluid capacitance value of a fluid path used for the delivery operation of the liquid drug based on the first pressure and the second pressure;
determine an intended liquid drug delivery amount; and
determine the delivery error amount of the liquid drug based on the first pressure, and the second pressure, the fluid capacitance value, and the intended liquid drug delivery amount.

19. The apparatus of claim 18, wherein the monitoring component indicates an over-delivery condition when the delivery error amount is greater than a first threshold and the monitoring component indicates an under-delivery condition when the delivery error amount is less than the second threshold.

20. The apparatus of claim 19, wherein the monitoring component is configured to generate the alert-alarm signal based on a determined severity of at least one of the over-delivery condition or the under-delivery condition.

* * * * *